US009631178B2

(12) United States Patent
Kieda et al.

(10) Patent No.: US 9,631,178 B2
(45) Date of Patent: Apr. 25, 2017

(54) HUMAN AND MURINE STEM-CELL LINES: MODELS OF ENDOTHELIAL CELL PRECURSORS

(75) Inventors: Claudine Kieda, Orleans (FR); Catherine Grillon, Darvoy (FR); Nathalie Lamerant-Fayel, Olivet (FR); Maria Paprocka, Wroclaw (PL); Agnieszka Krawczenko, Wroclaw (PL); Danuta Goszyk-Dus, Wroclaw (PL)

(73) Assignees: Centre National de la Recherche Scientifique—CNRS, Paris (FR); Ludwick Hirszfeld Institute of Immunology and Experimental Therapy Polish Academy, Wroclaw (PL)

( * ) Notice: Subject to any disclaimer, the term of this patent is extended or adjusted under 35 U.S.C. 154(b) by 0 days.

(21) Appl. No.: 13/521,715

(22) PCT Filed: Jan. 11, 2011

(86) PCT No.: PCT/FR2011/050045
§ 371 (c)(1),
(2), (4) Date: Oct. 5, 2012

(87) PCT Pub. No.: WO2011/086319
PCT Pub. Date: Jul. 21, 2011

(65) Prior Publication Data
US 2013/0040315 A1    Feb. 14, 2013

(30) Foreign Application Priority Data

Jan. 12, 2010    (FR) ...................................... 10 00111

(51) Int. Cl.
*C12N 5/071*    (2010.01)
*G01N 33/50*    (2006.01)
(52) U.S. Cl.
CPC ....... *C12N 5/0692* (2013.01); *G01N 33/5064* (2013.01); *G01N 33/5073* (2013.01)
(58) Field of Classification Search
USPC .................................. 435/7.21, 34, 354, 366
See application file for complete search history.

(56) References Cited

U.S. PATENT DOCUMENTS

2009/0004661 A1*    1/2009    Shetty et al. ...................... 435/6
2009/0104159 A1*    4/2009    Prosper et al. ............... 424/93.7
2009/0291061 A1*   11/2009    Riordan ................. A61K 45/06
424/85.2

OTHER PUBLICATIONS

Planat-Benard et al. "Plasticity of human adipose lineage cells towards endothelial cells: physiological and therapeutic perspectives", Circulation 109: 656-63, 2004.*
Schreiter et al. "Hematopoietic and endothelial progenitor cells from mouse adult testis derived stem cell lines", Blood 108 (11): p. 408A, XP009136489, 2006.*
Cao et al. "Human adipose tissue-derived stem cells differentiate into endothelial cells in vitor and improve postnatal neovascularization in vivo", Biochemical and Biophysical Research Communications 332: 370-379, 2005.*
Qui et al. "Postnatal neovascularization by endothelial progenitor cells immortalized with simian virus 40T antigen gene", International Journal of Oncology 28(4): 815-821, 2006.*
Kim et al. "Successful stem cell therapy using umbilical cord blood-derived multipotent stem cells for Buerger's disease and ischemic limb disease animal model", Stem Cells 24: 1620-26, 2006.*
Kawamoto et al. "Transplantation of endothelial progenitor cells for therapeutic neovascularization", Cardiovascular Radiation Medicine 3: 221-225, 2002.*
Zheng et al. "Proteomic analysis for the assessment of different lots of fetal bovine serum as a raw material for cell culture. Part IV. Application of proteomics to the manufacture of biological drugs", Biotechnology Progress 22(5): 1294-1300, 2006.*
Qui Hui-Ying et al., "Postnatal neovascularization by endothelial progenitor cells immortalized with the simian virus 40T antigen gene", International Journal of Oncology, Apr. 2006, vol. 28, No. 4, pp. 815-821.
Akeson, A.L. et al. "In Vitro Model for Developmental Progression from Vasculogenesis to Angiogenesis with a Murine Endothelial Precursor Cell Line, MFLM-4". Microvascular Research, vol. 61, No. 1, 75-86, 2001.
Arbab, A.S.et al. "Magnetic resonance imaging and confocal microscopy studies of magnetically labeled endothelial progenitor cells trafficking to sites of tumor angiogenesis" Stem Cells. 2006;24:671-678.
Asahara, T. et al. "Isolation of Putative Progenitor Endothelial Cells for Angiogenesis". Science 275, 964, 1997.
Bleiziffer, O. et al. "T17b murine embryonal endothelial progenitor cells can be induced towards both proliferation and differentiation in a fibrin matrix". J Cell Mol. Med. vol. 13, No. 5, May 2009, 926-935.
Case, J. et al. "Human CD34 (+) AC133 (+) VEGFR-2(+) cells are not endothelial progenitor cells but distinct, primitive hematopoietic progenitors". Experimental Hematolology. 2007, 35, 1109-1118.

(Continued)

*Primary Examiner* — Emily Cordas
(74) *Attorney, Agent, or Firm* — Arent Fox LLP

(57) ABSTRACT

The present invention relates to isolated human cells that are precursors of endothelial cells other than embryonic stem cells, to isolated murine cells that are precursors of endothelial cells, and to methods using same. In particular, the present invention relates to established cell lines of isolated human cells that are precursors of endothelial cells other than embryonic stem cells and established cell lines of isolated murine cells that are precursors of endothelial cells. The present invention can be used in particular in the medical and/or veterinary fields, in particular in the field of therapeutics and/or in the field of studies of cellular mechanisms.

11 Claims, 21 Drawing Sheets

(56) References Cited

OTHER PUBLICATIONS

Cipriani, P. et al.: "Impairment of Endothelial Cell Differentiation from Bone Marrow-Derived Mesenchymal Stem Cells—New Insight Into the Pathogenesis of Systemic Sclerosis". Arthritis & Rheumatism, vol. 56, No. 6, 1994-2004, Jun. 2007.
de Jonge-Peeters S.D. et al. "ABC transporter expression in hematopoietic stem cells and the role in AML drug resistance". Critical Review in Oncology/Hematology. 214-26, 2007.
Dome, B. et al. "Circulating endothelial cells, bone marrow-derived endothelial progenitor cells and proangiogenic hematopoietic cells in cancer: From biology to therapy". Critical Review in Oncology/Hematology, 2009, 69:108-1241.
Kieda, C. et al. "New Human Microvascular Endothelial Cell Lines with Specific Adhesion Molecules Phenotypes". Endothelium. 9: 247-261, 2002.
Kim, S. et al. "Endothelial Stem Cells and Precursors for Tissue Engineering: Cell Source, Differentiation, Selection, and Application". Tissue Engineering Part B, vol. 14, No. 1, 133-147, 2008.
Lin, Y. et al. "Origins of circulating endothelial cells and endothelial outgrowth from blood". The Journal of Clinical Investigation. Jan. 2000;105:71-77.
Madonna, R. et al. "In vitro neovasculogenic potential of resident adipose tissue precursors". Am J Physiol Cell Physiol 295: C1271-C1280, 2008.
Miyata, T. et al. "Platelet-Derived Growth Factor-BB (PGDF-BB) Induces Differenciation of Bone Marrow Endothelial Progenitor Cell-Derived Cell Line TR-BME2 Into Mural Cells, and Changes the Phenotype". Journal of Cellular Physiology, vol. 204, 948-955, 2005.
Peichev, M. et al. "Expression of VEGFR-2 and AC133 by circulating human CD34 (+) cells identifies a population of functional endothelial precursors". Blood. 2000;95:952-958.
Qiu, H. et al. "Postnatal neovascularization by endothelial progenitor cells immortalized with the simian virus 40T antigen gene". International Journal of Oncology, vol. 28, No. 4, 815-821, 2006.
Reinisch, A. et al. "Humanized large-scale expanded endothelial colony-forming cells function in vitro and in vivo". Blood. vol. 113, No. 26, 6716-6725, Jun. 2009.
Schreiter, J. et al. "Hematopoietic and Endothelial Progenitor Cells from Mouse Adult Testis Derived Stem Cell Lines". American Society of Hemotology, vol. 108, No. 11, part 1, 2006, p. 480.
Sharpe, E. et al. "The Origin and in Vivo Significance of Murine and Human Culture-Expanded Endothelial Progenitor Cells". American Journal of Pathology, vol. 168, No. 5, May 2006, 1710-1721.
Shi, Q. et al. "Evidence for Circulating Bone Marrow-Derived Endothelial Cells". Blood. 1998;92:362-367.
Slayton, W.B. et al. "The Role of the Donor in the Repair of the Marrow Vascular Niche Following Hematopoietic Stem Cell Transplant". Stem Cells. vol. 25,(11):2945-2955, Nov. 2007.
Suh, W. et al. "Transplantation of Endothelial Progenitor Cells Accelerates Dermal Wound Healing with Increased Recruitment of Monocytes/Macrophages and Neovascularization". Stem Cells. 2005; 23:1571-1578.
Szyda, A.. et al. "Optimization of a retroviral vector for transduction of human CD34 positive cells". Acta Biochimica Polonica. vol. 53, 815-823, 2006.
Tarnok, A. et al. "Phenotypes of Stem Cells from Diverse Origin". Cytometry Part A., vol. 77A, Dec. 6-10, 2009.
Yamahara, K. et al. "Potential use of endothelial progenitor cells for regeneration of the vasculature". The Advances in Cardiovascular Disease. 2009;3:17-27.
Yamamoto, H. et al. "Identification of two distinct populations of endothelial antigen expression from human umbilical cord blood". Ann Hematol, 87:87-95, 2008.

* cited by examiner

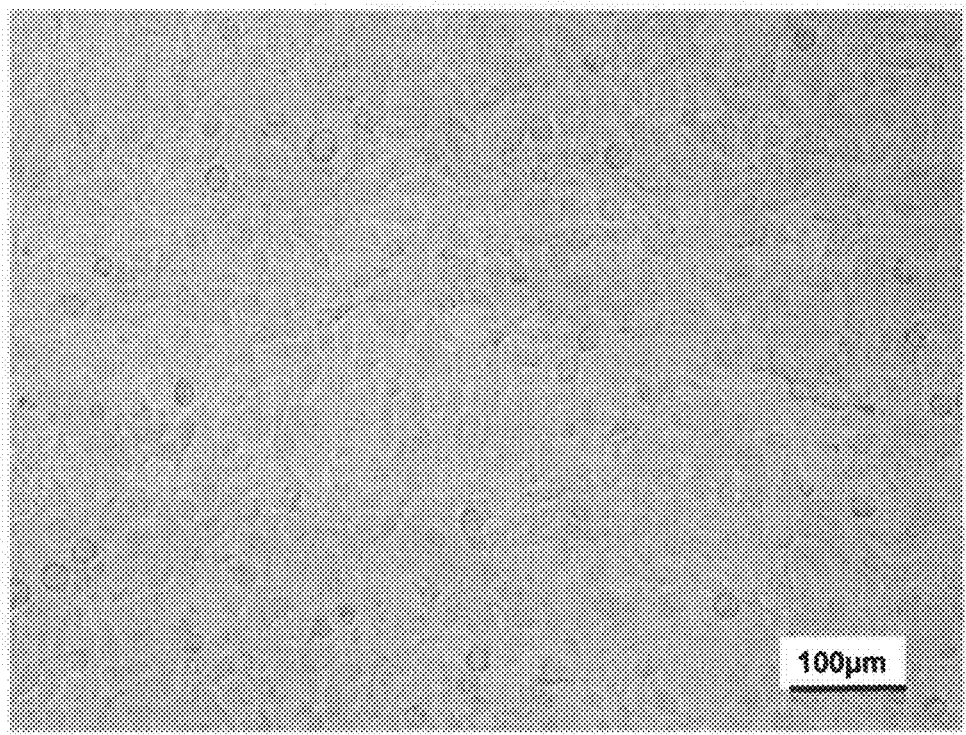
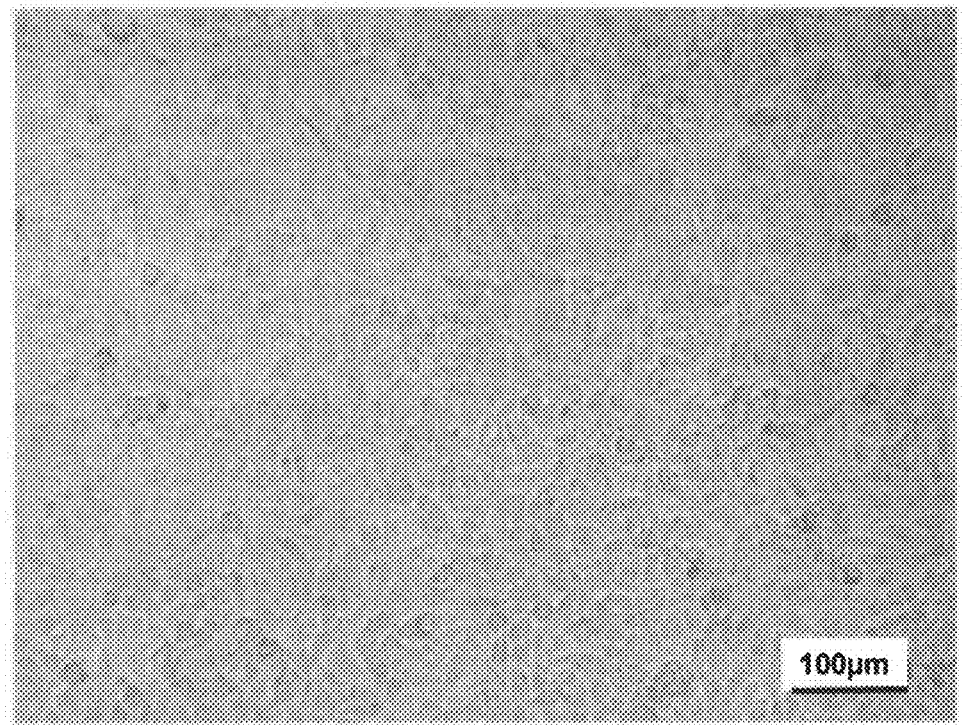
FIGURE 1

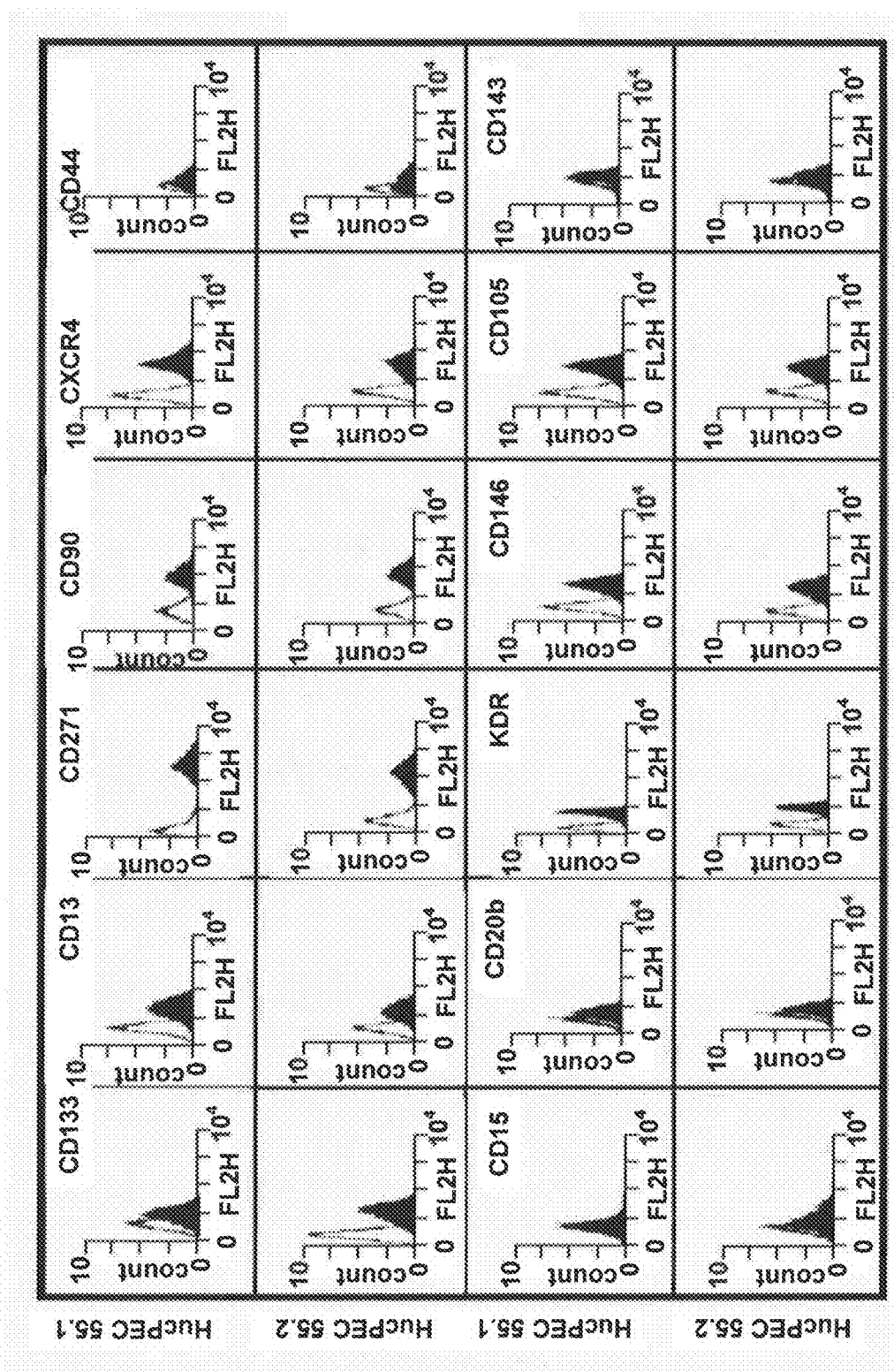
FIGURE 2 (1/2)

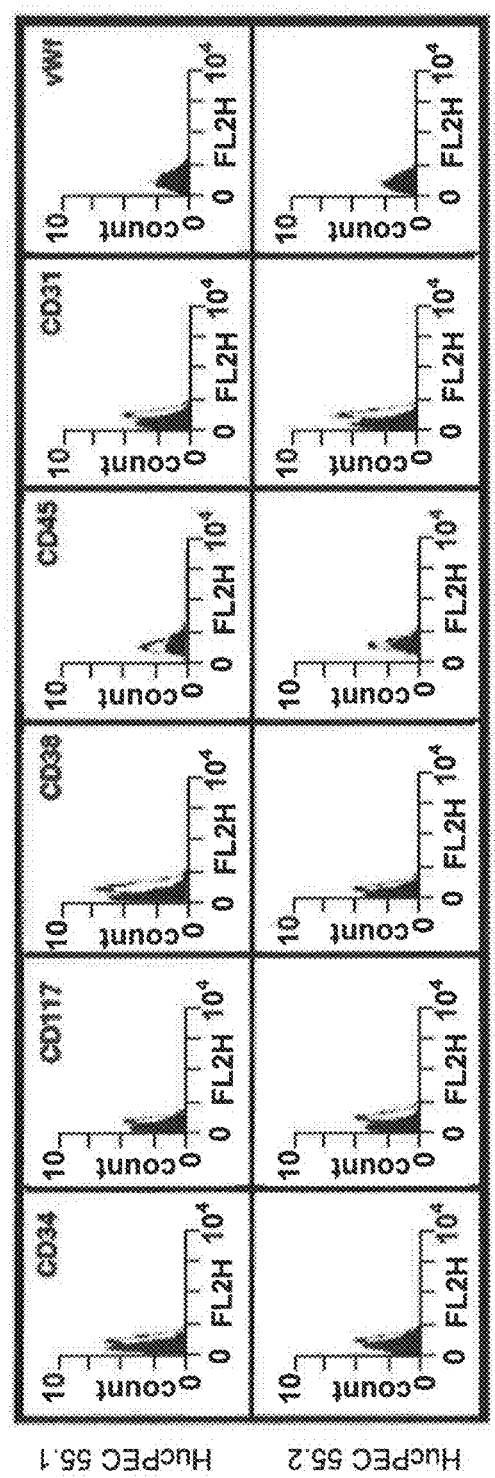
FIGURE 2 (2/2)

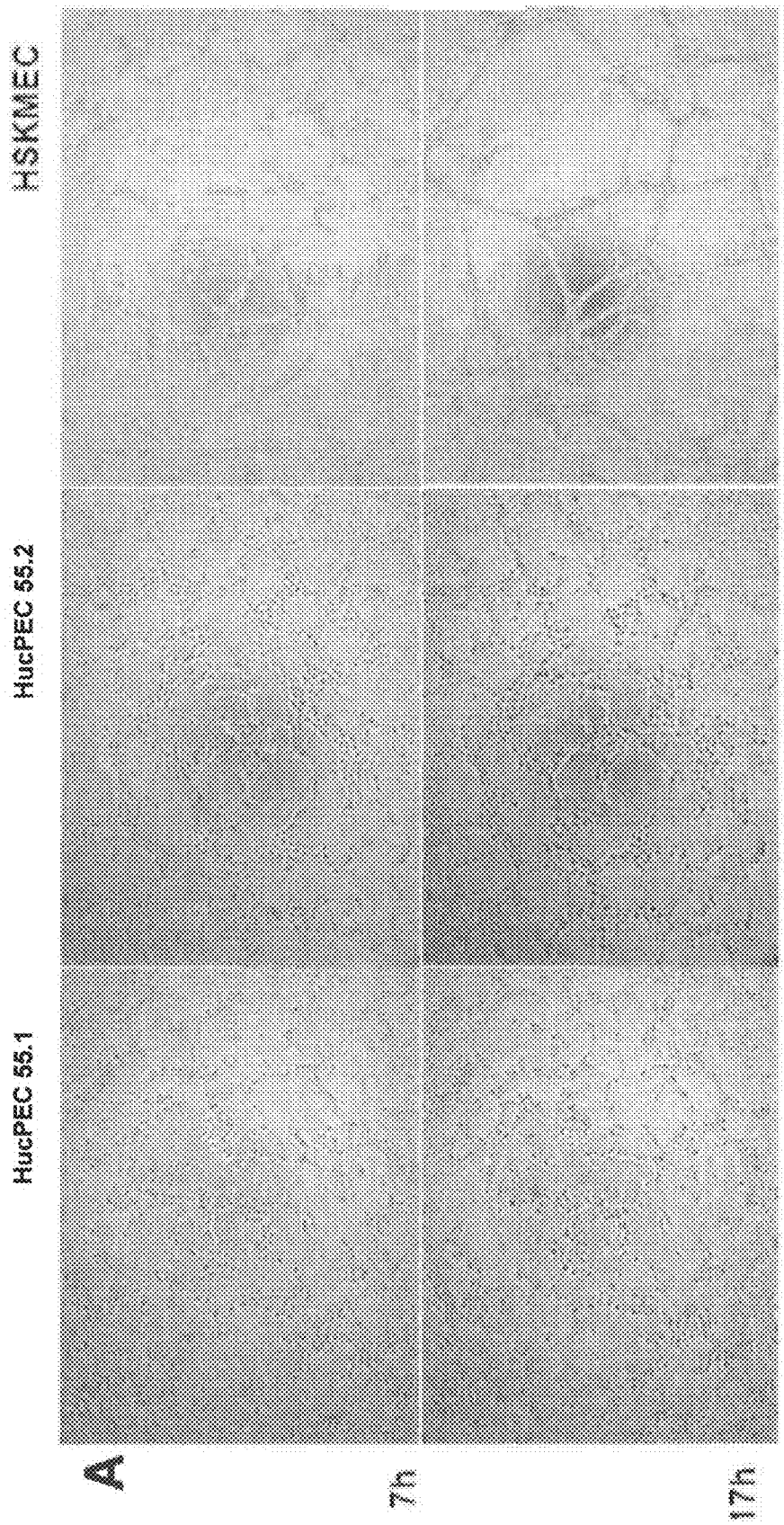
FIGURE 6 (1/2)

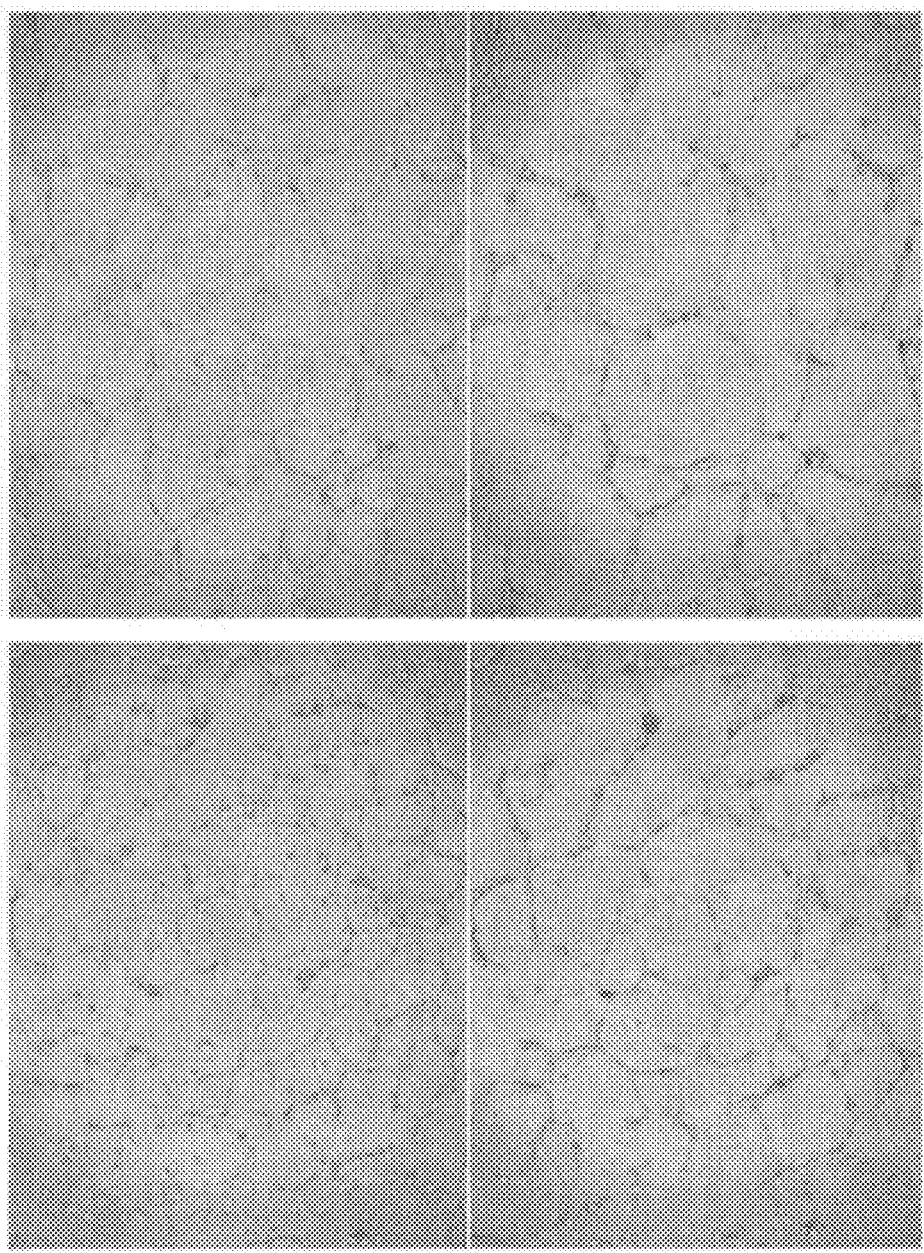
FIGURE 6 (2/2)

Expression of CCR5 in the MAgEC 10.5 and 11.5 cell lines

Expression of CCR10 in the MAgEC 10.5 and 11.5 cell lines

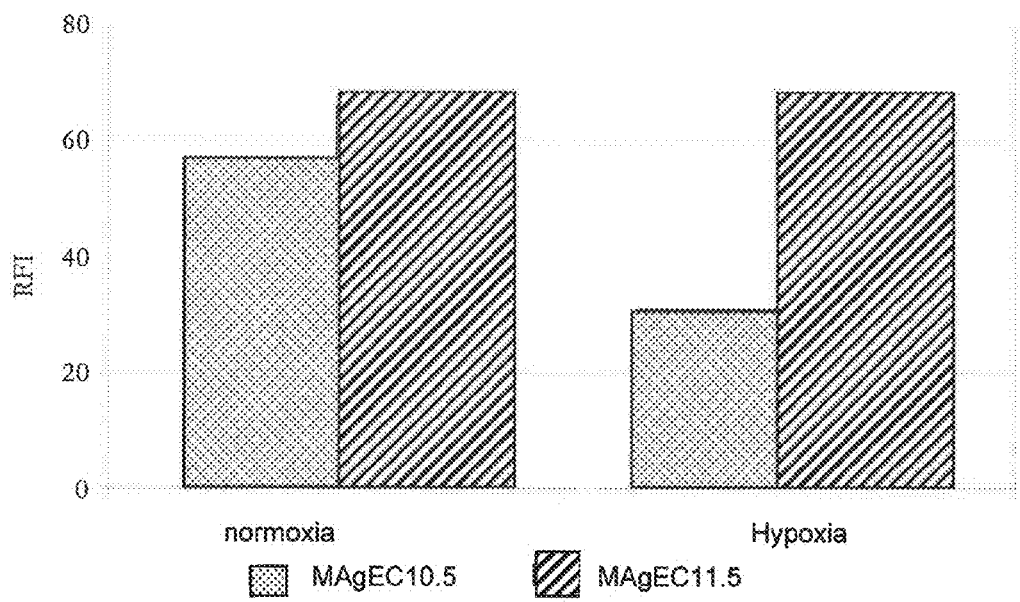
Figure 15
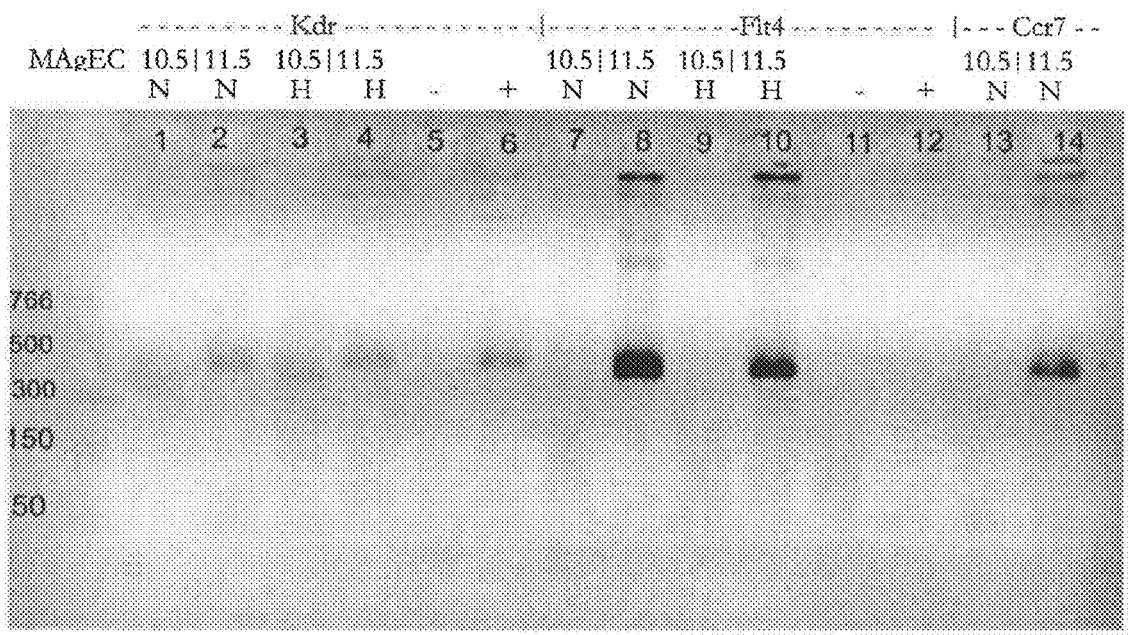
Figure 16 (1/2)

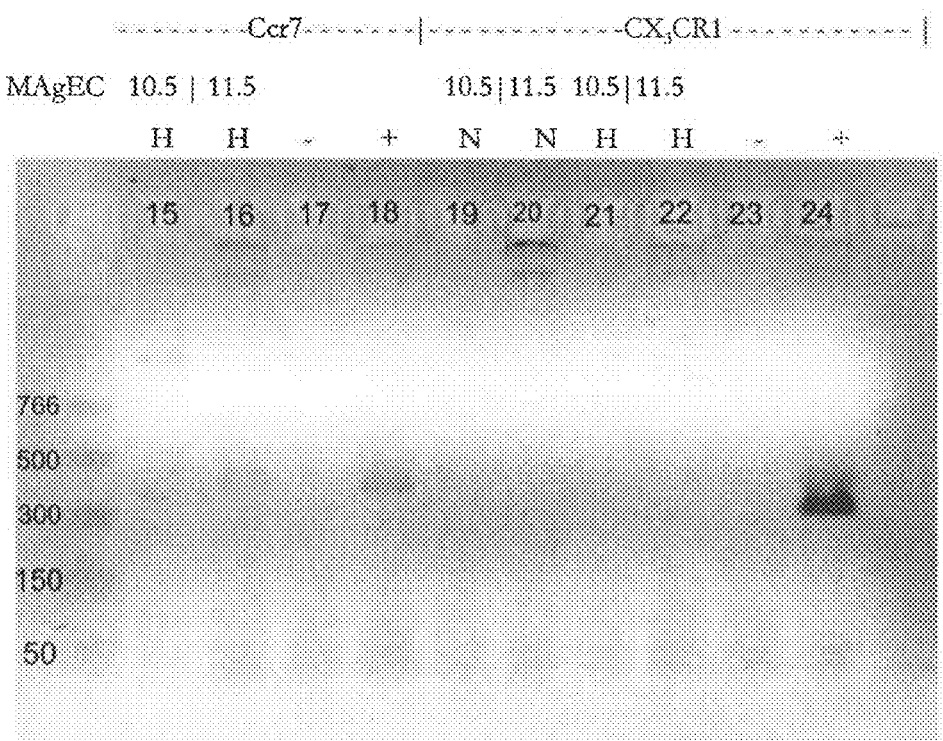
Figure 16 (2/2)
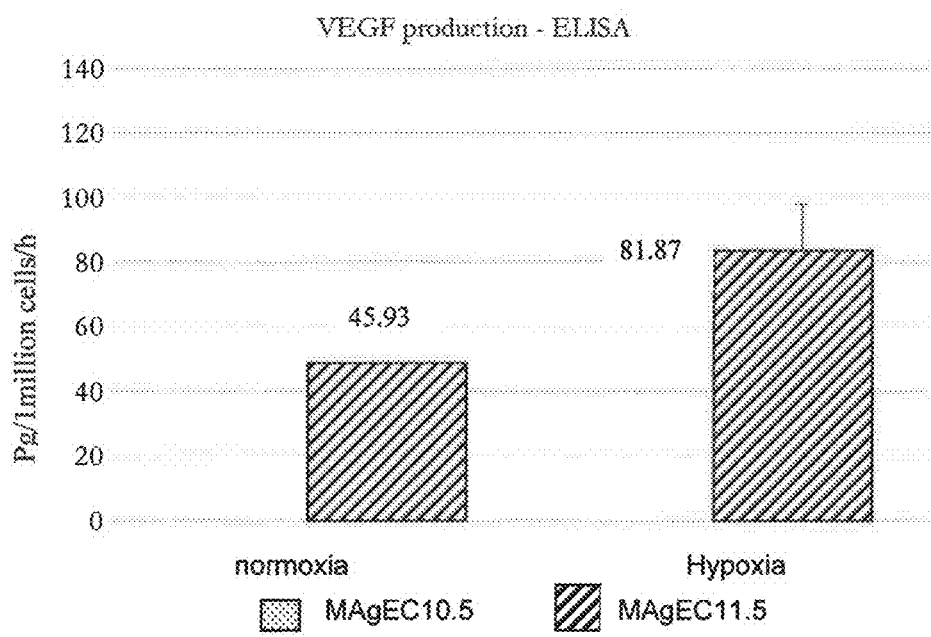
Figure 17

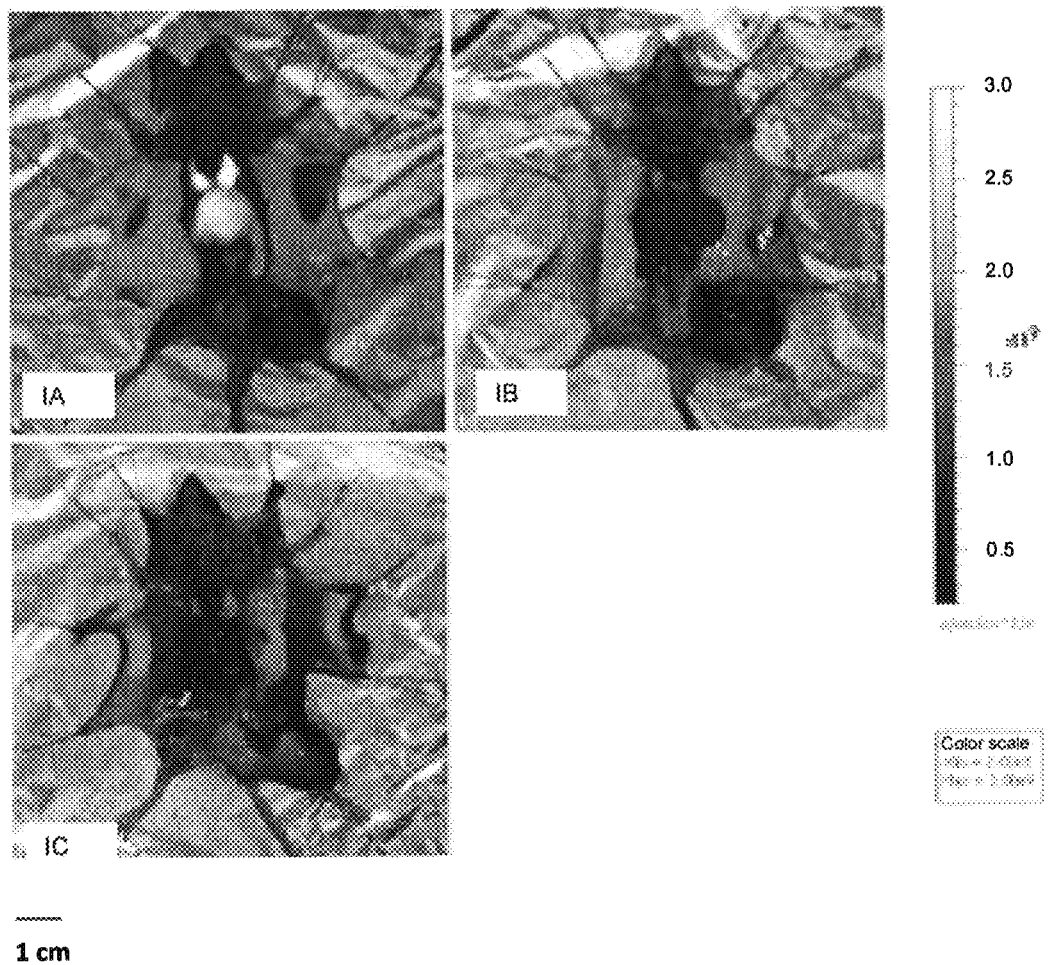
FIGURE 25 (1/2)

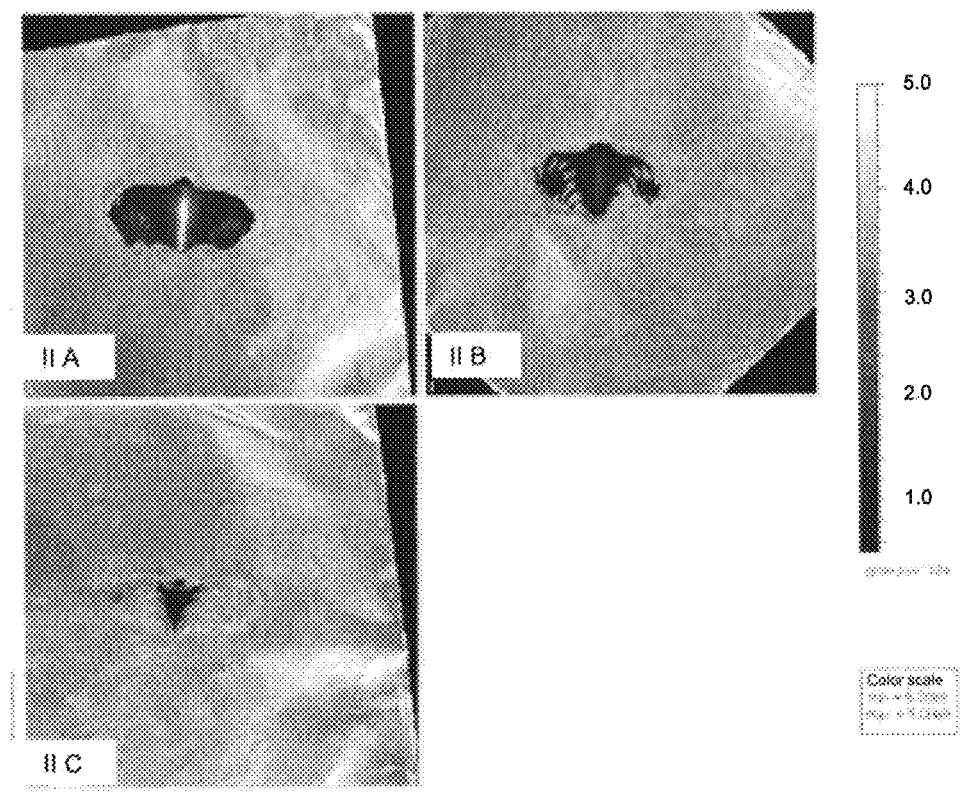
Figure 25 (2/2)

SEQUENCE LISTING

```
<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: primer MDR-1s

<400> SEQUENCE: 1
aagcttagta ccaaagaggc tctg                                            24

<210> SEQ ID NO 2
<211> LENGTH: 24
<212> TYPE: DNA
<213> ORGANISM: Artificial Sequence
<220> FEATURE:
<223> OTHER INFORMATION: primer MDR-1as

<400> SEQUENCE: 2
ggctagaaac aatagtgaaa acaa                                            24

<210> SEQ ID NO 3
<211> LENGTH: 20
<212> TYPE: DNA
<213> ORGANISM: Artificial Sequence
<220> FEATURE:
<223> OTHER INFORMATION: primer MDR3-s

<400> SEQUENCE: 3
agggcgactt tgaactgggc                                                 20

<210> SEQ ID NO 4
<211> LENGTH: 20
<212> TYPE: DNA
<213> ORGANISM: Artificial Sequence
```

```
<220> FEATURE:
<223> OTHER INFORMATION: primer MDR3-as

<400> SEQUENCE: 4
tttgcctgga tttagcagcg                                            20

<210> SEQ ID NO 5
<211> LENGTH: 25
<212> TYPE: DNA
<213> ORGANISM: Artificial Sequence
<220> FEATURE:
<223> OTHER INFORMATION: primer MRP1-s

<400> SEQUENCE: 5
agtgacctct ggtccttaaa caagg                                      25

<210> SEQ ID NO 6
<211> LENGTH: 25
<212> TYPE: DNA
<213> ORGANISM: Artificial Sequence
<220> FEATURE:
<223> OTHER INFORMATION: primer MRP1-as

<400> SEQUENCE: 6
gaggtagaga gcaaggatga cttgc                                      25

<210> SEQ ID NO 7
<211> LENGTH: 19
<212> TYPE: DNA
<213> ORGANISM: Artificial Sequence
<220> FEATURE:
<223> OTHER INFORMATION: primer BCRP-s

<400> SEQUENCE: 7
ttaggattga agccaaagg                                             19

<210> SEQ ID NO 8
<211> LENGTH: 21
<212> TYPE: DNA
<213> ORGANISM: Artificial Sequence
<220> FEATURE:
<223> OTHER INFORMATION: primer BCRP-as

<400> SEQUENCE: 8
taggcaattg tgaggaaaat a                                          21

<210> SEQ ID NO 9
<211> LENGTH: 24
<212> TYPE: DNA
<213> ORGANISM: Artificial Sequence
<220> FEATURE:
<223> OTHER INFORMATION: primer LRP-s

<400> SEQUENCE: 9
gtcttcgggc ctgagctggt gtcg                                       24

<210> SEQ ID NO 10
<211> LENGTH: 24
<212> TYPE: DNA
<213> ORGANISM: Artificial Sequence
<220> FEATURE:
<223> OTHER INFORMATION: primer LRP-as

<400> SEQUENCE: 10
cttggccgtc tcttgggggt cctt                                       24
```

```
<210> SEQ ID NO 11
<211> LENGTH: 20
<212> TYPE: DNA
<213> ORGANISM: Artificial Sequence
<220> FEATURE:
<223> OTHER INFORMATION: primer actin-s

<400> SEQUENCE: 11
ccagagcaag agaggcatcc                                               20

<210> SEQ ID NO 12
<211> LENGTH: 20
<212> TYPE: DNA
<213> ORGANISM: Artificial Sequence
<220> FEATURE:
<223> OTHER INFORMATION: primer actin-as

<400> SEQUENCE: 12
ctgtggtggt gaagctgaag                                               20

<210> SEQ ID NO 13
<211> LENGTH: 20
<212> TYPE: DNA
<213> ORGANISM: Artificial Sequence
<220> FEATURE:
<223> OTHER INFORMATION: sens primer CXCL16

<400> SEQUENCE: 13
agacagcaag aagcaccagg                                               20

<210> SEQ ID NO 14
<211> LENGTH: 20
<212> TYPE: DNA
<213> ORGANISM: Artificial Sequence
<220> FEATURE:
<223> OTHER INFORMATION: antisens primer CXCL16

<400> SEQUENCE: 14
cctctcccat gtcatcatcc                                               20

<210> SEQ ID NO 15
<211> LENGTH: 20
<212> TYPE: DNA
<213> ORGANISM: Artificial Sequence
<220> FEATURE:
<223> OTHER INFORMATION: sens primer SDF-1

<400> SEQUENCE: 15
gttcttcgag agccacatcg                                               20

<210> SEQ ID NO 16
<211> LENGTH: 20
<212> TYPE: DNA
<213> ORGANISM: Artificial Sequence
<220> FEATURE:
<223> OTHER INFORMATION: antisens primer SDF-1

<400> SEQUENCE: 16
atggcggagt gtctttatgc                                               20

<210> SEQ ID NO 17
<211> LENGTH: 20
<212> TYPE: DNA
<213> ORGANISM: Artificial Sequence
<220> FEATURE:
<223> OTHER INFORMATION: sens primer CX3CL1
```

```
<400> SEQUENCE: 17
tgcgacaaga tgacctcacg                                          20

<210> SEQ ID NO 18
<211> LENGTH: 20
<212> TYPE: DNA
<213> ORGANISM: Artificial Sequence
<220> FEATURE:
<223> OTHER INFORMATION: antisens primer CX3CL1

<400> SEQUENCE: 18
atcctgtgcc tcggaagttg                                          20

<210> SEQ ID NO 19
<211> LENGTH: 22
<212> TYPE: DNA
<213> ORGANISM: Artificial Sequence
<220> FEATURE:
<223> OTHER INFORMATION: sens primer 6Ckine

<400> SEQUENCE: 19
ggactgctgc cttaagtaca gc                                       22

<210> SEQ ID NO 20
<211> LENGTH: 21
<212> TYPE: DNA
<213> ORGANISM: Artificial Sequence
<220> FEATURE:
<223> OTHER INFORMATION: antisens primer 6Ckine

<400> SEQUENCE: 20
gctatcctct tgagggctgt g                                        21

<210> SEQ ID NO 21
<211> LENGTH: 23
<212> TYPE: DNA
<213> ORGANISM: Artificial Sequence
<220> FEATURE:
<223> OTHER INFORMATION: sens primer CTACK

<400> SEQUENCE: 21
ggctgagtga gtgagcatga tgg                                      23

<210> SEQ ID NO 22
<211> LENGTH: 20
<212> TYPE: DNA
<213> ORGANISM: Artificial Sequence
<220> FEATURE:
<223> OTHER INFORMATION: antisens primer CTACK

<400> SEQUENCE: 22
gggatgaaca cagacactgc                                          20

<210> SEQ ID NO 23
<211> LENGTH: 20
<212> TYPE: DNA
<213> ORGANISM: Artificial Sequence
<220> FEATURE:
<223> OTHER INFORMATION: sens primer Kdr

<400> SEQUENCE: 23
agagtgtgtc cctgttgtgc                                          20

<210> SEQ ID NO 24
```

```
<211> LENGTH: 20
<212> TYPE: DNA
<213> ORGANISM: Artificial Sequence
<220> FEATURE:
<223> OTHER INFORMATION: antisens primer Kdr

<400> SEQUENCE: 24
ggggtaggat ttccagatgc                                                 20

<210> SEQ ID NO 25
<211> LENGTH: 20
<212> TYPE: DNA
<213> ORGANISM: Artificial Sequence
<220> FEATURE:
<223> OTHER INFORMATION: sens primer Flt4

<400> SEQUENCE: 25
gagtgactcc ctggagatgc                                                 20

<210> SEQ ID NO 26
<211> LENGTH: 20
<212> TYPE: DNA
<213> ORGANISM: Artificial Sequence
<220> FEATURE:
<223> OTHER INFORMATION: antisens primer Flt4

<400> SEQUENCE: 26
tagcccgtct tgatgtctgc                                                 20

<210> SEQ ID NO 27
<211> LENGTH: 19
<212> TYPE: DNA
<213> ORGANISM: Artificial Sequence
<220> FEATURE:
<223> OTHER INFORMATION: sens primer CCR7

<400> SEQUENCE: 27
aaacccagga aaacgtgc                                                   19

<210> SEQ ID NO 28
<211> LENGTH: 21
<212> TYPE: DNA
<213> ORGANISM: Artificial Sequence
<220> FEATURE:
<223> OTHER INFORMATION: antisens primer CCR7

<400> SEQUENCE: 28
rgtagacgcc aaagatccag g                                               21

<210> SEQ ID NO 29
<211> LENGTH: 20
<212> TYPE: DNA
<213> ORGANISM: Artificial Sequence
<220> FEATURE:
<223> OTHER INFORMATION: sens primer CXC3R1

<400> SEQUENCE: 29
tcttcatcac cgtcatcagc                                                 20

<210> SEQ ID NO 30
<211> LENGTH: 20
<212> TYPE: DNA
<213> ORGANISM: Artificial Sequence
```

```
<220> FEATURE:
<223> OTHER INFORMATION: antisens primer CXC3R1

<400> SEQUENCE: 30
gatgcggaag tagcaaaagc                                                        20
```

HUMAN AND MURINE STEM-CELL LINES: MODELS OF ENDOTHELIAL CELL PRECURSORS

FIELD OF TECHNOLOGY

The present invention relates to isolated human cells that are endothelial cell precursors other than embryonic stem cells, to isolated murine cells that are endothelial cell precursors representing a model of differentiation in both cases. The present invention also relates to methods using them. In particular, the present invention relates to established cell lines of isolated human cells that are endothelial cell precursors other than embryonic stem cells and to established cell lines of isolated murine cells that are endothelial cell precursors.

The present invention finds applications in the medical and/or veterinary field, in particular in therapeutics, and/or in the area of investigation of cellular mechanisms, for example cellular repair, angiogenesis or targeting mechanisms.

In the following description, the references given in square brackets ([ ]) refer to the list of references given at the end of the text.

PRIOR ART

The endothelial cell precursor cells have been the subject of numerous scientific studies and publications for many years. In fact, since stem cells were identified, many studies have been undertaken in order to identify the specific markers of stem cells, as well as the various factors that may induce differentiation and/or specialization of these cells. Prior to differentiation, stem cells can give rise to any cells. They can differentiate and become, for example, precursors of specialized cells. One of the best known types of stem cells is hematopoietic stem cells. These cells have been much studied owing to their potential involvement in diseases such as acute myeloid leukemia, and tumor growth, as presented in the documents Arbab A S, Pandit S D, Anderson S A, et al. "Magnetic resonance imaging and confocal microscopy studies of magnetically labeled endothelial progenitor cells trafficking to sites of tumor angiogenesis." Stem Cells. 2006; 24:671-678 [1]; de Jonge-Peeters S D, Kuipers F, de Vries E G, Vellenga E. "ABC transporter expression in hematopoietic stem cells and the role in AML drug resistance." Crit Rev Oncol Hematol. 2007 June; 62(3):214-26. Epub 2007 Mar. 23. [2]; Slayton W B, Li X M, Butler J, Guthrie S M, Jorgensen M L, Wingard J R, Scott E W. "The role of the donor in the repair of the marrow vascular niche following hematopoietic stem cell transplant." Stem Cells. 2007 November; 25(11):2945-55 [3]. One of the main objectives of these studies was to identify the various cellular precursors, for example endothelial cell precursors.

Various studies have proposed cells with different markers that can induce the formation of endothelial cells.

Endothelial progenitor cells (EPCs) can be found in several tissues as well as in the blood circulation, as shown in the document Dome B, Timar J, Ladanyi A, et al. "Circulating endothelial cells, bone marrow-derived endothelial progenitor cells and proangiogenic hematopoietic cells in cancer: From biology to therapy." Crit Rev Oncol Hematol. 2009; 69:108-1241 [4]. These cells are endowed with the capacity to actively find sites where endothelial damage has occurred, adhere to the damaged surface and differentiate into endothelial cells so as to reconstitute the vascular integrity; these various effects are presented in the following documents: Yamahara K, Itoh H. "Potential use of endothelial progenitor cells for regeneration of the vasculature." Ther Adv Cardiovasc Dis. 2009; 3:17-27. [5]; Suh W, Kim K L, Kim J M, et al. "Transplantation of endothelial progenitor cells accelerates dermal wound healing with increased recruitment of monocytes/macrophages and neovascularization." Stem Cells. 2005; 23:1571-1578. [6]; Slayton W B, Li X M, Butler J, et al. "The role of the donor in the repair of the marrow vascular niche following hematopoietic stem cell transplant." Stem Cells. 2007; 25:2945-2955 [7]. This aspect of targeting is particularly important for tissue repair, for example myocardial tissue damaged after an infarction, but also pathological processes such as tumor growth or retinopathy [1].

Evidence for endothelial cell precursor cells was found more than ten years ago, but their identification, their characterization and their true potential for differentiation are still controversial.

One of the main problems in identifying endothelial cell precursor cells arises from the absence of specific markers and the lack of strict criteria for defining them, as well as their functions.

Currently there are no established cell lines in the prior art for endothelial cell precursor cells. Thus, no cell line of endothelial cell precursor cells is available, regardless of the original species.

Endothelial cell progenitors or putative angioblasts were isolated for the first time from peripheral human blood by selection on magnetic beads based on expression of the CD347 antigen on the cell surface. In vitro, these cells were capable of differentiating into endothelial cells. In animal models of ischemia, endothelial cell precursor cells are incorporated in sites of active angiogenesis, as presented in the document Shi Q, Rafii S, Wu M H, et al. "Evidence for circulating bone marrow-derived endothelial cells." Blood. 1998; 92:362-367 [8].

Endothelial cell precursor cells are very difficult to identify as it is a rare population both in bone marrow and in the circulating blood.

In order to proceed to separation of these cells, selection was effected, in the prior art, via surface expression of putative markers of endothelial cell precursor cells. For example, a combination of the markers CD133 and/or CD34 and sometimes of specific markers of endothelial cells such as VEGFR-2 (CD309), VE-cadherin (CD144) and the melanoma cell adhesion molecule (M-CAM, CD146) were used for separating stem cells and cellular precursors as described in Lin Y, Weisdorf D J, Solovey A, et al. "Origins of circulating endothelial cells and endothelial outgrowth from blood." J Clin Invest. 2000; 105:71-77 [9]; Peichev M, Naiyer A J, Pereira D, et al. "Expression of VEGFR-2 and AC133 by circulating human CD34(+) cells identifies a population of functional endothelial precursors." Blood. 2000; 95:952-958. [10]. The endothelial cell precursor cells were then propagated in various conditions and characterized by in vitro and/or in vivo methods which led to contradictory results.

After the separation step, several markers (CD45, CD13, CD31, CD105, CD144, CD202b, Ulex Agglutinin-1 (UEA-1)) have usually been evaluated in order to characterize the populations of cells obtained and discriminate the putative EPCs from hematopoietic stem cells (HSCs). The endothelial and hematopoietic lines both originate from a common progenitor: the hemangioblast, and the closer the progenitors, the greater their similarities and therefore it will be more difficult to distinguish between the lines.

Recently, the common leukocyte antigen CD45 was suggested as a marker to aid in distinguishing between hematopoietic and endothelial lines, since it is not expressed in embryonic hemangioblasts and is acquired during differentiation only by the cells of the hematopoietic line. It has also been demonstrated that in adults, only the CD34+ CD45− cells are capable of differentiating into endothelial cell precursor cells whereas the CD34+ CD45+ cells differentiate into cells of the EC type expressing the additional monocytic marker CD14+.

Moreover, progenitor cells that have the following markers: CD34+AC133+ and VEGFR2+ are not endothelial cell precursor cells but precursor cells of hematopoietic cells as indicated in Case J, Mead L E, Bessler W K, Prater D, White H A, Saadatzadeh M R, Bhavsar J R, Yoder M C, Haneline L S, Ingram D A "Human CD34+AC133+VEGFR-2+ cells are not endothelial progenitor cells but distinct, primitive hematopoietic progenitors." Exp Hematol. 2007 October; 35(10):1479-80 [11].

Therefore clearly there are doubts concerning the markers of endothelial cell precursor cells and there is a real need for identifying and isolating endothelial cell precursor cells that can be used in therapy.

Moreover, just like the hematopoietic stem cells, the endothelial cell precursors are known to contribute to the generation of vessels in adults and to the modulation of postnatal vascularization. These cells are also known to have a role in tumor growth through the generation of new vessels. In fact, studies have shown, using special devices, that precursor cells can be recruited in tumors and/or tissue lesions in order to produce vessels, thus enabling these tumors to grow and/or participating in the regeneration of injured tissues as described in Arbab A S, Pandit S D, Anderson S A et al. [1]; Asahara T, Murohara T, Sullivan A, Silver M, van der Zee R, Li T, Witzenbichler B, Schatteman G, Isner J M. "Isolation of putative progenitor endothelial cells for angiogenesis." Science. 1997 Feb. 14; 275(5302): 964-7 20 [12]. However, no "model" of endothelial cell precursor cell line exists in the prior art.

There is a real need to find at least one model/established cell line that overcomes the flaws, drawbacks and obstacles of the prior art, in particular cell lines making it possible to study cellular mechanisms, for example those involved in the generation of vessels, methods for identifying molecules acting on addressing of cells, formation of new vessels and thus making it possible to control the manner of recruitment, and molecules involved in and/or inhibiting this recruitment of cells and/or formation of vessels, moreover making it possible to reduce the costs and improve the treatments of disorders involving endothelial cell precursor cells.

There is therefore also a real need to identify, isolate and make available endothelial cell precursor cells, which are notably usable in therapy, for example in cellular therapy for treating tissue lesions by specifically targeting the injured tissue and/or other disorders associated for example with genetically deficient cells thus making it possible to control, improve and reduce the cost of the treatments.

DESCRIPTION OF THE INVENTION

The present invention in fact makes it possible to solve the aforementioned problems and drawbacks of the prior art, by supplying isolated endothelial cell precursor cells.

The inventors are the first to have succeeded in isolating human endothelial cell precursor cells other than embryonic stem cells, and murine endothelial cell precursor cells.

Furthermore, the inventors have immortalized said cells and have obtained established cell lines, i.e. immortalized, stable, nontumorigenic cell lines whose characteristics are identical from one generation to another. A definition of an established cell line is given in the book Genes IV, by Benjamin Leuvin, page 1133, 6th edition, De Boeck University.

The present invention therefore relates to an isolated human endothelial cell precursor cell, other than embryonic stem cells, comprising the clusters of differentiation (CD) 133, 13, 271, 90 202b, 309, 146, 105 and 143; and not comprising the clusters of differentiation CD31 and CD45.

The inventors elaborated lines after carrying out the culture and stabilization of the phenotype of various cells that correspond to this definition of the invention. These cells were deposited, under the Budapest Treaty, at the National Collection of Cultures of Microorganisms (Collection Nationale de Cultures de Microorganismes, CNCM), Institut Pasteur, 25 rue du Docteur Roux, 75724 Paris cedex 15, France. These are for example isolated human cells that are endothelial cell precursors other than embryonic stem cells deposited at the Collection Nationale de Cultures de Microorganismes (CNCM), Institut Pasteur, 25 rue du Docteur Roux, 75724 Paris cedex 15, France on Aug. 18, 2009 under CNCM numbers No. 1-4220 (HucPEC 55.1) and No. 1-4221 (HucPEC 55.2).

They are for example isolated murine cells that are endothelial cell precursors. In particular, it can be an isolated murine cell that is a precursor of endothelial cells other than embryonic stem cells deposited at the Collection Nationale de Cultures de Microorganismes (CNCM), Institut Pasteur, 25 rue du Docteur Roux, 75724 Paris cedex 15, France on Aug. 18, 2009 under CNCM numbers No. I-4222 (MAgEC 10.5) and No. I-4223 (MAgEC 11.5).

Among the many advantages that the inventors have demonstrated for the present invention, the aforementioned cells make it possible to identify molecules that can induce differentiation and/or specialization. In particular, the inventors have demonstrated that certain molecules can stimulate the cells to cause angiogenesis.

Thus, the present invention also relates to a method of screening molecules that can induce differentiation and/or specialization of an isolated cell as described above comprising the steps of:
  introducing the molecule to be screened into a medium that is suitable for culture of said cell,
  introducing at least one isolated cell into said medium,
  culturing said cell in said medium for a sufficient time to allow its differentiation and/or its specialization,
  taking at least one cell resulting from said culture,
  observing the differentiation and/or specialization of said cell by phenotypic observation of the cell and/or by detecting differentiation markers.

According to the present invention, the step of introducing the molecule to be screened can be performed before, simultaneously with and/or after the step of introducing at least one isolated cell.

In the present invention, "differentiation" means a mechanism by which the cell will acquire particular characteristics. For example, differentiation can lead to production of cells of the vascular type, pigmented or unpigmented epithelial cells, cells such as osteocytes, muscle cells, adipocytes etc.

In the present invention, "specialization" means a method by which the cell will become specialized, i.e. the cell will be a differentiated cell, for example endothelial cells of vessels, circulating endothelial cells, endothelial cells of bone marrow, spleen, thymus, of secondary lymphoid organs, of peripheral organs for example endothelial cells of the liver, lungs, kidneys or brain.

In the present, "molecule to be screened" means a chemical molecule, a peptide and/or any molecule known by a person skilled in the art. For example, the molecule to be screened can be a molecule that is commercially available and/or for which we wish to know its effect on the cells of the present invention. They can also be molecules that are known to induce cellular differentiation or specialization, for example growth factors such as the members of the family of platelet derived growth factors (PDGF), PDGF1, PDGF2, vascular growth factor (VEGF: "vascular endothelial growth factor"), vascular permeability factor (VPF), members of the family of epidermal growth factors (EGF), transforming growth factor (TGFa "transforming growth factor a"), members of the family of fibroblast growth factors (FGF), members of the family of insulin growth factors (IGF), differentiation factors, for example the interleukins IL3, IL6, 8, IP 10, VEGF, angiogenin, recombinant cytokines, for example stem cell recombinant factor (rh SCF: "stem cell factor"), recombinant granulocyte macrophage colony stimulating factor (rh GM-CSF). They can also be targeted therapeutic genes, any active molecule known in the prior art and/or any medicinal product given in the Vidal 2009 dictionary (registered trademark).

In the present, "medium suitable for culture" means any medium known by a person skilled in the art for culture of cells. It can for example be a liquid or solid medium. It can, for example, be commercially available media, for example a medium of the type aMEM, EBM-2, marketed by the company CLONETICS®, Lonza, Saint Beauzire, France, the media Basals from the company PROMOCELL®. A person skilled in the art will, on the basis of his general knowledge, easily be able to adapt and/or supplement the media, if necessary, for culture of the cells. For example, a medium EBM®-2 marketed by the company CLONETICS® (Lonza, Saint Beauzire, France) can be supplemented with 10% of fetal bovine serum marketed by the company HYCLON®, Longan, Utah, USA and at least one growth factor described in the document, such as ECGS (endothelial cell growth supplement) and/or for differentiation described in the document (VEGF).

According to a particular embodiment of the method of the invention, said molecules induce differentiation and/or specialization leading to angiogenesis. These molecules can be for example pro- or anti-angiogenesis molecules.

In the present, the culture step can be carried out at a temperature between 20 and 40° C., preferably at 37° C.

In the present, cell culture can be carried out in any container known by a person skilled in the art, for example Petri dishes, 6-well, 24-well, or 96-well plates, test tubes, incubators, for example "rollers", cultures on supports such as CYTODEX® beads, FALCON® plastic boxes and other makes.

In the present case, the sampling step can be carried out by any method known by a person skilled in the art. For example, sampling can be performed using a pipette, a sampling device, for example a sampling tube, a liquid sampler with a valve, a tube for sampling by aspiration.

In the present context, phenotypic observation can be performed by any method known by a person skilled in the art. For example, it can be performed by direct observation, by observation with a microscope, for example an electron microscope, electron microscope, scanning electron microscope, inverted microscope, phase-contrast microscope, fluorescence microscope, confocal microscope, video microscope.

Advantageously, phenotypic observation can be performed by video microscopy, which can make the method of the invention quantitative.

Phenotypic characterization can be performed by investigating the fixation of specific antibodies, optionally labeled and/or detected by a second antibody directed against the immunoglobulin molecule in question, and fluorescent. The labeling can be detected by flow cytofluorometry.

In the present, differentiation markers can be detected by any means known by a person skilled in the art, for example by means of specific dyes, specific antibodies of said differentiation markers such as presented in the document for cytochemical labeling, for example commercially available antibodies, for example monoclonal antibodies, polyclonal antibodies, for example mouse monoclonal antibodies marketed by the company SIGMA®, the company Becton Dickinson Biosciences, by fluorometric detection using labeled antibodies and/or an enzymatic reaction.

Advantageously, according to the present invention, the step of identification of the phenotype and/or of the markers makes it possible to know the effect of the screened molecule on the isolated cultured cell.

The present invention also relates to a kit for carrying out the method described above comprising:

at least one isolated cell according to the invention, and means for detecting cellular differentiation and/or specialization.

In the present invention, a detecting means can be any means known by a person skilled in the art permitting for example visual observation of the cells, for example an optical detecting means, for example a microscope as described above, for example an optical detecting means for detecting differentiation markers for example an antibody against a differentiation marker and/or any means known by a person skilled in the art making it possible to detect cellular differentiation and/or specialization. It can for example be the antibodies described above.

The present invention also relates to a cell culture comprising at least one isolated cell described above.

In the present, the cell culture can be for example any cell culture comprising at least one cell of the invention, for example a human or murine precursor endothelial cell according to the invention.

The inventors discovered that the cells isolated according to the invention are capable of targeting pathological sites as well as regenerating new endothelial tissues. In particular, the inventors discovered that the cells according to the invention are capable of specifically targeting tumors and/or injured tissues. Thus, the cells of the invention can supply therapeutic molecules and/or genes at pathological sites. The cells of the invention can also for example target injured and/or necrotic tissues in order to regenerate said tissues.

Thus, the present invention relates to a cell isolated according to the invention for use as a medicinal product and/or for use in the manufacture of a medicinal product.

Preferably, the medicinal product is intended for treating genetically deficient cells, tissue lesions, damage to endothelial tissues, necrotic tissues. For example, the medicinal product can be intended for treating infarction, vascular lesions, sites of injury due to diabetes.

According to the present invention, the isolated cells of the invention can also be used as transporters of genes and/or of at least one therapeutic molecule to a pathological site. Expression of the gene may depend on the environmental conditions of the pathological site.

Advantageously, addressing of genes and/or of at least one therapeutic molecule to a pathological site additionally makes it possible to improve the efficacy of the molecule by direct and targeted action making it possible for example to reduce the amount required to obtain the therapeutic effect and reduce the appearance of side effects and/or reduce the side effects associated with the molecules.

In the present text, "pathological site" means for example any tissue and/or cellular abnormality, for example it can be a tissue lesion, necrotic tissues, genetically deficient cells, tumors and/or any site of proliferation of a pathology. Preferably, it is a tissue lesion, necrotic tissues, genetically deficient cells, tumors, wounds, or ischemia.

In the present text, "therapeutic molecule" means any molecule known by a person skilled in the art that can be used for treating a pathology in the medical and/or veterinary field, it can for example be any molecule given in the Vidal 2009 dictionary.

The present invention therefore advantageously finds application in therapeutics, for example veterinary and/or medical, for example for treating tissue lesions, administering therapeutic molecules, but also in the pharmaceutical field for identifying molecules that can induce differentiation and/or specialization of endothelial cell precursor cells etc.

Other advantages may appear to a person skilled in the art on reading the following examples, illustrated by the appended figures, given for purposes of illustration.

BRIEF DESCRIPTION OF THE DRAWINGS

FIG. 1 is a photograph showing the morphology of two cell lines HucPEC 55.1 (A) and HucPEC 55.2 (B).

FIG. 2 shows flow cytometry histograms of the cell lines HucPEC 55.1 and HucPEC 55.2 with positive markers (A) and negative (B). The empty curves represent the isotypical controls and the filled curves represent the labeled cells. The ordinate shows the number of cells (counts) and the abscissa shows the fluorescence (FLH2).

FIG. 4A shows a photograph in which the transcript codes for MDR1; FIG. 4B shows a photograph in which the transcript codes for MDR3; FIG. 4C shows a photograph in which the transcript codes for MRP1; FIG. 4D shows a photograph in which the transcript codes for BCRP, FIG. 4E shows a photograph in which the transcript codes for LRP and FIG. 4F shows a photograph in which the transcript is that of the gene of β-actin. In the photographs, line M corresponds to the markers of molecular weights; line 1 to the HucPEC 55.1 cells; line 2 to the HucPEC 55.2 cells.

FIGS. 6 A and B show photographs of the formation of pseudovessels on MATRIGEL® as a function of time, by HucPEC 55.1, HucPEC 55.2 and HSkMEC cells.

FIG. 15 is a bar chart showing the expression of the marker CXCR4 in cell lines MAgEC 10.5 (dotted lines) and 11.5 (cross-hatched) measured by flow cytofluorometry as a function of conditions of normoxia or hypoxia. The ordinate shows the relative intensity of fluorescence and the abscissa shows the conditions of normoxia or hypoxia.

FIG. 16 shows photographs of gels of mRNA transcripts coding for the genes Kdr (columns 1 to 4), Flt4 (columns 7 to 10), CCR7 (columns 13 to 16), $CX_3CR1$ (columns 19 to 22) in the MAgEC 10.5 and 11.5 cells as a function of conditions of normoxia (N) or hypoxia (H). The columns − and + correspond respectively to the negative and positive controls.

FIG. 17 is a bar chart showing production of VEGF measured by ELISA by the cell lines MAgEC 10.5 (dotted lines) and 11.5 (cross-hatched) as a function of conditions of normoxia or hypoxia. The ordinate shows the amount of VEGF determined after establishing a calibration curve, in pg (picograms) per million cells and the abscissa shows the conditions of normoxia or hypoxia.

FIG. 25 shows images obtained by near infrared fluorescence imaging 7 days after injection of MAgEC 11.5 cells. Images IA, IB and IC are whole body images, images IIA, IIB and IIC show the images of the sternum and of the bones of the chest.

EXAMPLES

Example 1

Figure 3:
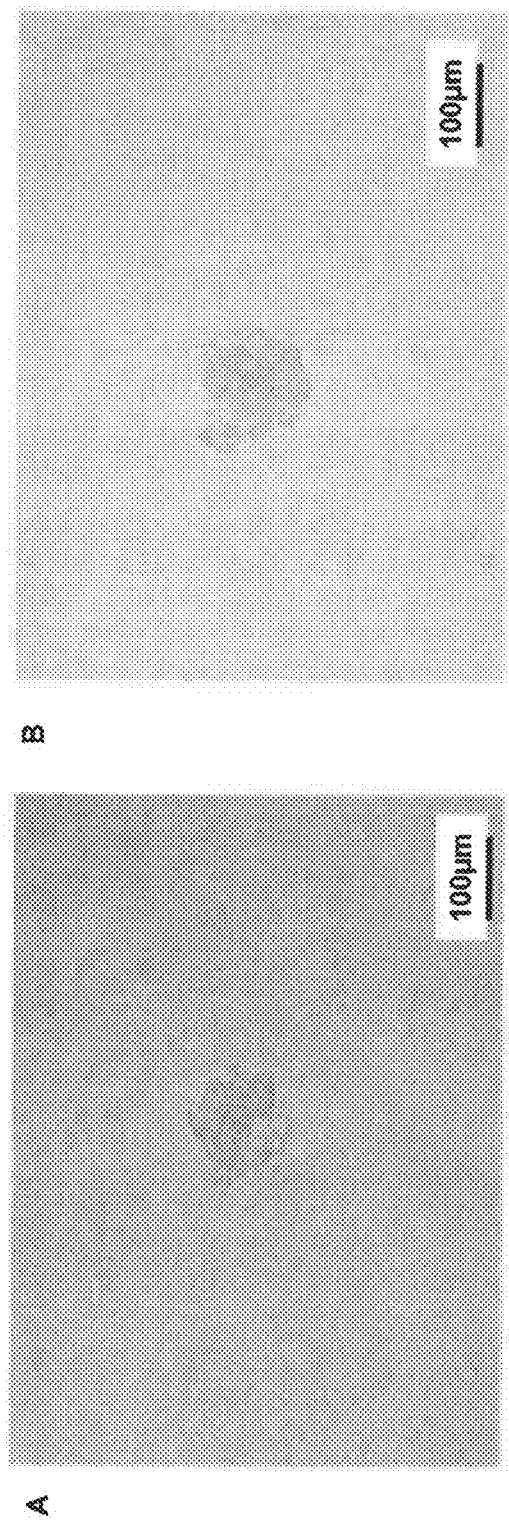
FIG. 3 is a photograph showing the spheroidal morphology of cell lines HucPEC 55.1 and HucPEC 55.2 cultured in a hematopoietic cell differentiation medium.

Production and Characterization of Isolated Human Endothelial Cell Precursor Cells A Material and Methods
A.1 Blood Samples Blood samples were taken from human umbilical cord blood. The cord blood was collected from normal full-term births at the "Chair of Obstetrics and Gynecology" of the Wroctaw medical university. The umbilical vein was pierced with a size 17 needle attached to a sealed recovery bag system containing a solution of citrate phosphate dextrose as anticoagulant for blood bags (marketed by MACO Pharma, Wroctaw, Poland). The volume collected was on average 50-110 ml from one placenta. Written informed consent was obtained from all the mothers prior to labor and childbirth. The protocols for taking samples of human umbilical cord blood were approved by the Bioethics Commission at Wroclaw Medical University.

A.2. Isolation of Mononuclear Cells

The mononuclear cells of umbilical cord blood were isolated by density gradient centrifugation using LYMPHOFLOT® density gradient at a concentration of 1.077 g/ml (marketed by the company Biotest, Dreieich, Germany). The layer of mononuclear cells was collected, the cells were washed twice with 1 mM of ethylenediaminetetraacetic acid (EDTA) in phosphate-buffered saline (PBS) and stored frozen in liquid nitrogen until use.

A.3 Culture of the Mononuclear Cells and Immortalization Thereof

The isolated mononuclear cells ($1\times10^6$ ml) were cultivated in tissue culture dishes, the plastic of which is covered with a layer of human fibronectin BIOCOAT® marketed by the company Becton Dickinson Biosciences, Grenoble, France) at 37° C. in an atmosphere of 95% air and 5% $CO_2$. The medium used for cell culture was EBM®-2 marketed by the company CLONETICS®, Ionza, Saint Beauzire, France, supplemented with 10% of fetal bovine serum marketed by the company HYCLON®, Longan, Utah, USA; and suitable growth factors and differentiation factors. After culture for 3 days, the medium was supplemented with the supernatant from cells (50% vol/vol) of retroviral cell lines TE FLY GA hTERT obtained in our laboratory as described in Szyda A, Paprocka M, Krawczenko A, et al. Optimization of a retroviral vector for transduction of human CD34 positive cells. Acta Biochim Pol. 2006; 53:815-823 [13].

After culture for 3 weeks, 2 clones of proliferating cells were replicated. The cells were cultured for 1 month in EBM-2 medium, supplemented with 10% FCS (HYCLON®) and growth factors: rhSCF (SIGMA®), rhSCGF (100 ng/mL), (AbD PEPROTECH®, rhFlt-3 ligand (R&D SYSTEMS®), rh VEGF (R&D SYSTEMS® or SIGMA®).

The two clones obtained were designated HucPEC 55.1 and HucPEC 55.2.

Photographs of the growing cells were taken with the AXIOVERT® S Zeiss microscope marketed by the company Jena, Germany equipped with a FINE PIX® 5602 digital camera marketed by the company Fuji Film.

A.4. Immunolabeling of the Cell Lines HucPEC 55.1 and HucPEC 55.2

The phenotype of the cultured cells was analyzed using uncoupled anti-Willebrand factor rabbit polyclonal antibodies marketed by the company SIGMA® and the following mouse monoclonal antibodies: anti-CD133 coupled to phycoerythrin (PE) and anti-CD271 coupled to fluorescein isothiocyanate (FITC) marketed by the company Miltenyi Biotec, Paris, France, anti-CD105 coupled to PE, uncoupled anti-CD143, anti-CD146, anti-CXCR4, anti-hVEGFR2 and anti-CD202 marketed by the company R&D SYSTEMS®, anti-CD13 coupled to PE, anti-CD34, anti-CD38, anti-CD54, anti-CD90 marketed by the company Becton Dickinson Biosciences, anti-CD45 coupled to FITC, uncoupled anti-CD44 and anti-CD15s marketed by the company Becton Dickinson Biosciences, anti-CD31 coupled to FITC marketed by the company SIGMA®.

All the directly labeled antibodies were used at a rate of $1\times10^5$ cells/sample, suspended in phosphate-buffered saline (PBS) supplemented with 1% FCS at a suitable concentration. The cells are incubated with the antibodies for 30 min at 4° C. After incubation, the cells were washed carefully. The controls are carried out with nonspecific immunoglobulins, of the same isotype.

Similarly, three unlabeled antibodies were used for $1\times10^5$ cells/sample suspended in PBS supplemented with 1% FCS. Incubation is carried out for 30 min at 4° C. After incubation, the cells were washed carefully and the anti-mouse or anti-rabbit secondary antibodies labeled with FITC were applied subsequently for 30 min at 4° C.

Before analysis by fluorescence-activated cell sorter (FACS), the cells were washed in PBS. The controls were carried out with rabbit or mouse immunoglobulins of the same isotype.

Prior to detection of CD143 and of von Willebrand factor, the cells were fixed and permeabilized with 2% of paraformaldehyde and 0.2% of saponin in a solution of PBS for 10 min for intracellular labeling.

The cells were analyzed by flow cytometry using FACSCALIBUR® marketed by the company Becton Dickinson, CA, USA. The data were acquired and recorded for 5000-10000 events using CELLQUEST® software marketed by the company Becton Dickinson and presented to be analyzed in the form of histograms using WINMDI 2.7 software.

A.5. Capacity of the Cell Lines HucPEC 55.1 and HucPEC 55.2 to Grow and Differentiate into Hematopoietic Cells in a Semi-Solid Medium The capacity of the HucPEC 55.1 and HucPEC 55.2 cells to grow and differentiate into hematopoietic cells was evaluated using METHOCULT® GF H4434 marketed by the company StemCell Technologies Inc. Vancouver, Canada, containing the following recombinant cytokines: rhSCF (50 ng/ml), rhGM-CSF (10 ng/ml), rhIL3 (10 ng/ml) and recombinant erythropoietin (3 units/ml).

$10^3$ cells of the two cell lines tested were suspended in 1 ml of semi-solid medium METHOCULT® marketed by the company StemCell and transferred to 24-well plates. After culture for 7 days, photographs were taken of the clusters of growing cells.

A.6 Detection of the mRNAs in the Cellular Precursors of the HucPEC 55.1 and HucPEC 55.2 Lines by Reverse Transcription and Polymerase Chain Reaction (RT-PCR)

The total cellular RNA was isolated from $2.5 \times 10^6$ cells using the MINIKIT RNEASY PROTECT® marketed by the company Qiagen, Courtaboeuf, France. The first strand of cDNA synthesized was made by reverse transcription of 1 µg of total RNA using OMNISCRIPT REVERSE TRANSCRIPTASE® marketed by the company Qiagen. The polymerase chain reaction (PCR) for detecting the mRNAs of MDR1, MDR3, MRP1, BCRP and LRP as well as of β actin (guardian gene) was carried out using specific primers and the PCR conditions shown in Table 1.

TABLE 1

| Primers | SEQ ID NO | Nucleotide sequence | Conditions for PCR |
|---|---|---|---|
| MDR-1s | 1 | 5'-AAGCTTAGTACCAAAGAGGCTCTG-3' | 37 cycles of 94° C., 1 min; 58° C.m 1 min; 72° C., 1 min product obtained: 243 bp |
| MDR-1as | 2 | 5'-GGCTAGAAACAATAGTGAAAACAA-3' | |
| MDR3-s | 3 | 5'-AGGGCGACTTTGAACTGGGC-3' | 35 cycles of [94° C., 1 min; 60° C., 1 min; 72° C., 2 min], product obtained: 268 bp |
| MDR3-as | 4 | 5'-TTTGCCTGGATTTAGCAGCG-3' | |
| MRP1-s | 5 | 5'-AGTGACCTCTGGTCCTTAAACAAGG-3 | 35 cycles of [94° C., 1 min; 56° C., 1 min; 68° C., 1 min], product obtained: 657 bp |
| MRP1-as | 6 | 5'-GAGGTAGAGAGCAAGGATGACTTGC-3' | |
| BCRP-s | 7 | 5'-TTAGGATTGAAGCCAAAGG-3' | 35 cycles of [94° C., 40 s; 51° C., 1 min; 72° C., 1 min], product obtained: 446 bp |
| BCRP-as | 8 | 5'-TAGGCAATTGTGAGGAAAATA-3' | |
| LRP-s | 9 | 5'-GTCTTCGGGCCTGAGCTGGTGTCG-3' | 33 cycles of [94° C., 45 s; 55° C., 45 s; 72° C., 45 s], product obtained: 240 bp |
| LRP-as | 10 | 5'-CTTGGCCGTCTCTTGGGGGTCCTT-3' | |
| β actin-s | 11 | 5'-CCAGAGCAAGAGAGGCATCC-3' | 28 cycles of [94° C., 30 s; 55° C., 45 s; 72° C., 60 s], product obtained: 450 bp |
| β actin-as | 12 | 5'-CTGTGGTGGTGAAGCTGAAG-3' | |

A.7. Secretion of Various Cytokines by the Cell Lines HucPEC 55.1 and HucPEC 55.2

The secretion of cytokines was evaluated using the test with cytometric beads marketed by the company Becton Dickinson Biosciences. The following molecules were tested: interferon inducible protein 10 (IP-10), interleukin 6 (IL6), interleukin 8 (IL8), vascular endothelial growth factor (VEGF), angiogenin.

The supernatants of the cell lines HucPEC 55.1 and HucPEC 55.2 were collected after culture for 16 h either in normoxia (20% $O_2$) or in hypoxia (1% $O_2$) and stored frozen at −80° C. before using them.

The experiments were conducted in accordance with the manufacturer's protocol. About 300 beads were analyzed for each cytokine. The flow cytometry analyses of the labeling of the beads were performed using LSR® marketed by the company Becton Dickinson and the results were analyzed using the FCAP® test software marketed by the company Becton Dickinson.

A.8. Formation of Pseudovessels

The MATRIGEL® matrix marketed by the company Becton Dickinson Biosciences was diluted to 1/2 in OPTIMEM® base medium marketed by the company Invitrogen, Cergy Pontoise, France, at 4° C., distributed in 96-well microplates in a volume of 50 µl and left to polymerize at 37° C. for 30 min. The cells ($1.2 \times 10^4$ cells) of the HSkMEC lines (human skin microvascular cells) were obtained according to the method described in Kieda et al.

"New human microvascular endothelial cell lines with specific adhesion molecules phenotypes." Endothelium. 2002; 9(4):247-61 [14]. The HucPEC 55.1 and HucPEC 55.2 cells were seeded on microplates coated with MATRIGEL® matrix marketed by the company Becton Dickinson Biosciences in a volume of 100 µl and the cultures were conducted either in conditions of normoxia (20% $O_2$) or in conditions of hypoxia (1% $O_2$). The photographs were taken with an inverted microscope (AXIOVERT® 200M marketed by the company Zeiss, Le Pecq, France) equipped with an AXIO-CAM® high-resolution digital camera marketed by the company Zeiss, Le Pecq, France) connected to a computer running the AXIOVISION® acquisition software marketed by the company Zeiss. The direct, real-time visualization of the formation of the pseudo-vessels was monitored for 24 h.

B. Results

Two clones of proliferating cells were obtained after transduction of the mononuclear blood cells from human umbilical cord with a supernatant of the cell line TE FLY GA hTERT [13], producing retroviruses containing the gene of reverse transcriptase of human telomerases. The transductions were performed on 4 different samples of mononuclear blood cells from umbilical cord, cultivated in the same conditions, in the presence of a mixture of growth promoting factors. Two clones were obtained and were designated HucPEC 55.1 and HucPEC 55.2. The morphology of the two cell lines is shown in FIG. 1

B.1. Determination of the Immunophenotype of the Two Cell Lines HucPEC 55.1 and HucPEC 55.2

The two cell lines were first analyzed for expression of the markers of the precursor cells/stem cells and for the markers of the endothelial cells, comprising growth factor receptors and selected adhesion molecules as shown in FIG. 2A. The two cell lines express CD133, which is known to be a general marker of normal and neoplastic stem cells. They also express CD13 (marker of hematopoietic stem cells), CD271 (marker of nonhematopoietic stem cells) and CD90 (marker of mesenchymal stem cells). The two cell lines were positive for expression of CXCR4 and weakly positive for CD44 and CD15s, which can be expressed both on stem cells and on endothelial cells. The cells also express typical markers of endothelial cells: CD202b, VEGFR2, CD146, CD105 and express CD143 weakly. The markers that are not expressed by these cell lines are grouped together as shown in FIG. 2B. The two lines HucPEC 55.1 and HucPEC 55.2 were negative for CD34, CD117, CD38 and CD45, which suggests that they are not of hematopoietic origin. They did not express CD31 and vWf, markers of differentiated endothelial cells.

B.2. Capacity of the Cell Lines HucPEC 55.1 and HucPEC 55.2 for Growth and Differentiation into Hematopoietic Cells in a Semi-Solid Medium The two cell lines were cultivated in a semi-solid medium supplemented with growth factors and hematopoietic differentiation factors to evaluate their capacity for differentiating into hematopoietic cells. The two cell lines are capable of growing in a semi-solid medium, but do not differentiate into hematopoietic cells. After culture for 7 to 9 days, the cells form compact multicellular spheroids. They do not show any sign of differentiation into erythrocytes, granulocytes or monocytes, as can be seen in FIG. 3.

This experiment demonstrates that the cells isolated are therefore not precursor cells of hematopoietic cells.

B.3. Expression of the Multidrug Resistance mRNA Transcripts Detected by RT-PCR

Figure 4:
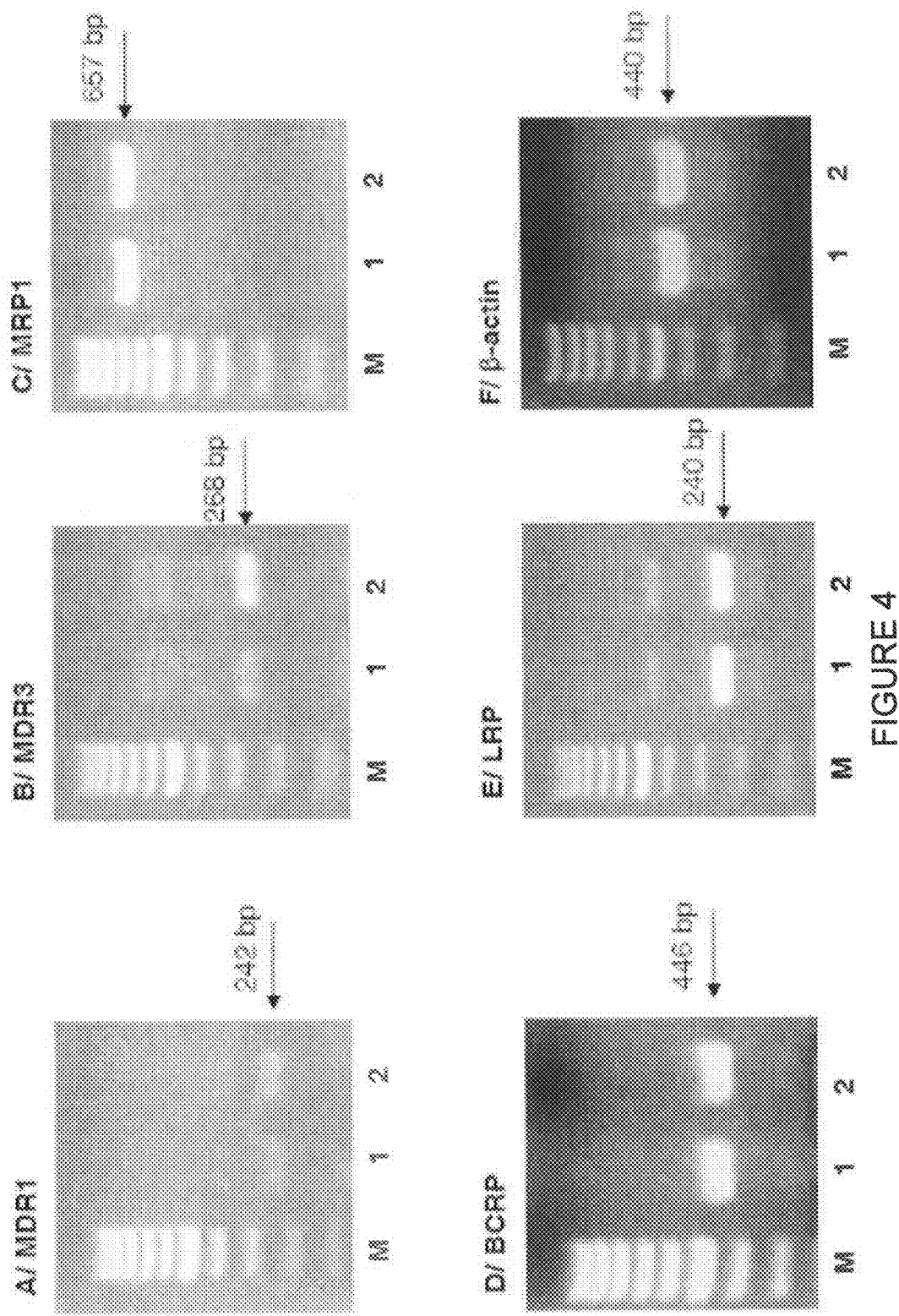
FIG. 4 shows photographs of gels of mRNA transcripts coding for multidrug resistance (MDR) genes.

A reverse transcriptase polymerase chain reaction (RT-PCR) of the mRNAs coding for the multidrug resistance proteins was used for monitoring the expression of their genes in the lines HucPEC 55.1 and HucPEC 55.2. Expression of the gene products for MDR1, MDR3, MRP1, BCRP and LR is presented in FIG. 4. The mRNAs of all the multidrug resistance proteins are present in the two cell lines at similar levels, with the exception of MDR3, which seems be expressed at a higher level in the HucPEC 55.2 line compared to the HucPEC 55.1 line.

B.4. Secretion of Cytokines by the Cell Lines HucPEC 55.1 and HucPEC 55.2

Figure 5:
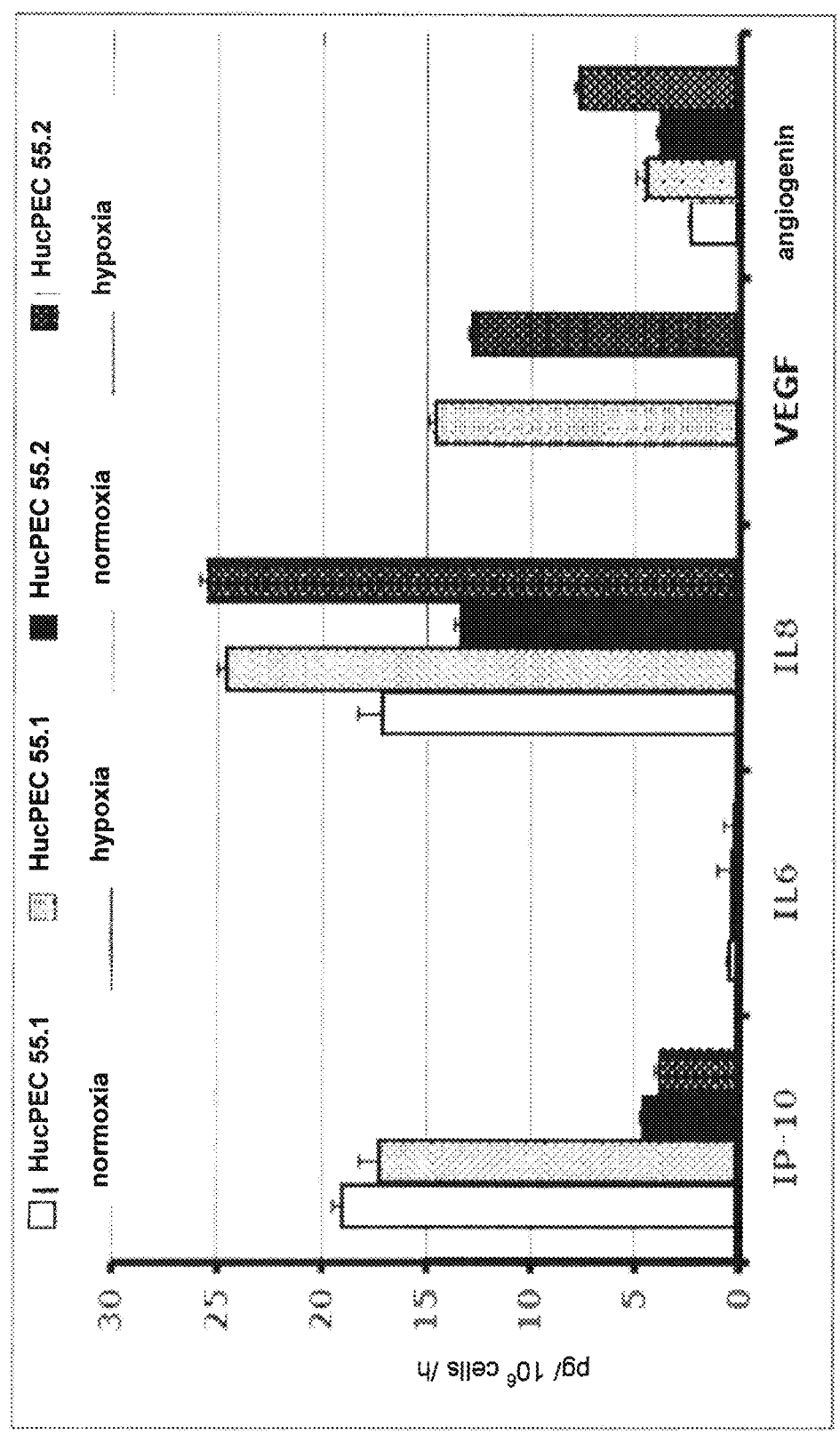
FIG. 5 shows a diagram of the secretion of cytokines by the HucPEC 55.1 and HucPEC 55.2 cells in conditions of hypoxia or normoxia. The ordinate shows the amount of factors secreted as a function of the amount of cells and time, and the abscissa indicates the various cytokines secreted.
Figure 7:
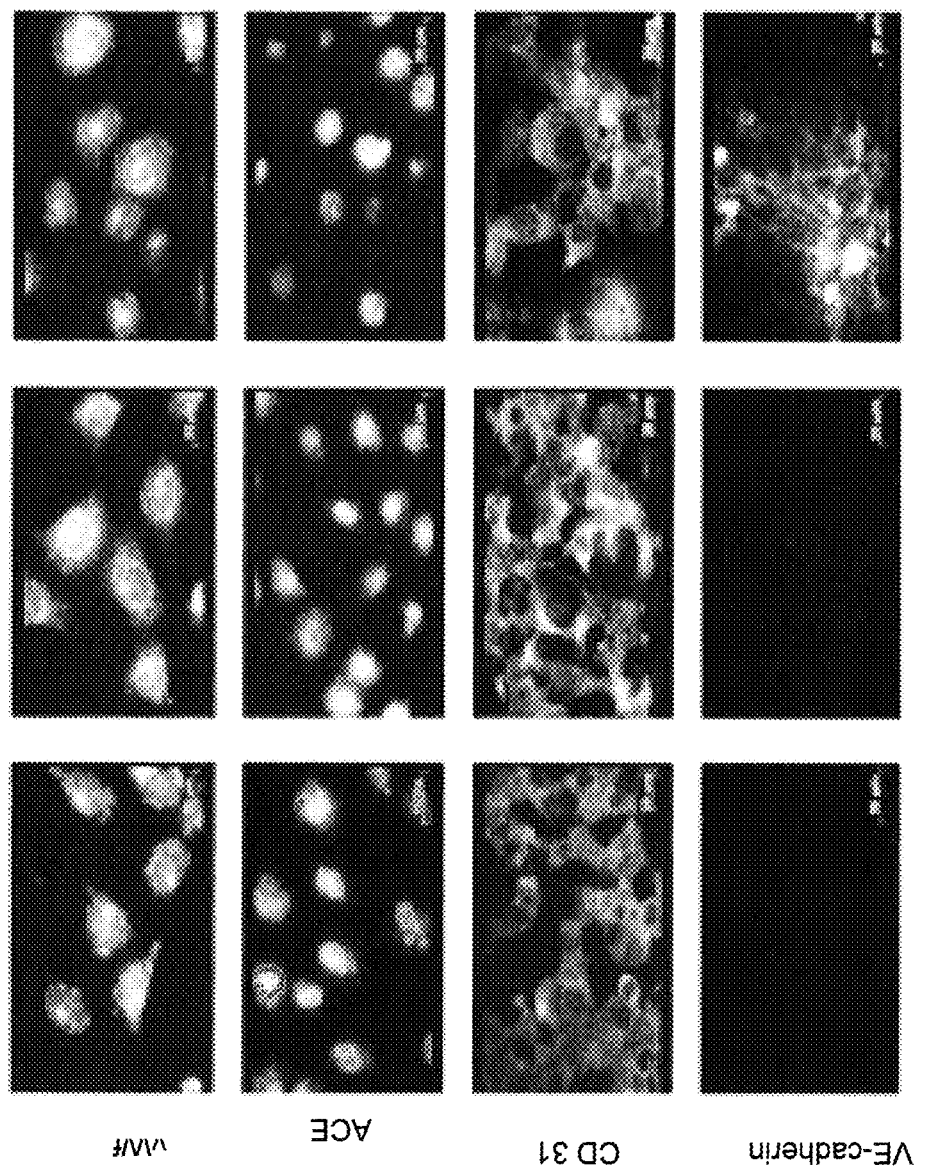
FIG. 7 shows photographs of the detection of specific markers: VE-cadherin, cluster of differentiation CD31, angiotensin converting enzyme (ACE), von Willebrand vascular factor (vWf) as a function of feline endothelial cell precursor cells and of time AGM 10.5 days, AGM 11.5 days.

The cytometric test on beads was used for evaluating the secretion of the selected cytokines (IP-10, IL6, IL8, VEGF and angiogenin) by the HucPEC 55.1 and HucPEC 55.2 cells growing in normoxic and hypoxic conditions. FIG. 5 shows that changing the oxygen partial pressure has an influence on the production of proangiogenic cytokines at variable points by the two cell lines. In fact, the production of proangiogenic cytokines IL8 and angiogenin increased significantly in hypoxia. The two cell lines did not produce VEGF in normoxia, but expression of this proangiogenic factor was induced by hypoxia in the two cell lines. IP10, which is an antiangiogenic cytokine, was produced at much higher levels by HucPEC 55.1 compared to HucPEC 55.2 and was not altered by hypoxia.

B.5. Angiogenic Properties of the Cell Lines HucPEC 55.1 and HucPEC 55.2

The two cell lines were tested for their angiogenic potential and rearrangement into pseudo-vessels on a semisolid matrix. The kinetics of this rearrangement to structures of the tube type was compared in hypoxia (1% $O_2$) versus normoxia. FIG. 6A shows that in normoxia, the two lines HucPEC 55.1 and HucPEC 55.2 are capable of beginning the angiogenic process in a manner comparable to the HSkMEC reference line, which is a differentiated microvascular endothelial cell line derived from the skin. This result clearly demonstrates that the cells have joined together to form a network. The network developed in less than 7 hours, for the cell lines HucPEC 55.1 and HucPEC 55.2, then it stopped. Regarding the HSkMECs line, its development took 17 hours.

After 7 hours, the cell lines HucPEC 55.1 and HucPEC 55.2 remained where they were and began to proliferate. The hypoxic conditions effectively accelerated the process of tube formation for the HucPEC 55.2 cells, as is shown in FIG. 6B. This process was also accelerated for the HucPEC 55.1 line, although it remained slower than for HucPEC 55.2. Besides acceleration, hypoxia also caused more complete differentiation toward formation of structures of the vessel type, which was not achieved in normoxia by any of the cell lines HucPEC 55.1 and HucPEC 55.1 and HucPEC 55.2.

As demonstrated in this example, the established cell lines HucPEC 55.1 and HucPEC 55.2 are endothelial cell precursor cells, which have angiogenic properties and have a shorter development time than the known cell lines, permitting faster proliferation.

Example 2

Production and Characterization of Isolated Murine Cells that are Endothelial Cell Precursors A Material and Methods
A1. Isolation of the Cells The cells were isolated from the Aorta Gonad Mesonephros (AGM) region of C57Bl6 embryos 10.5 and 11.5 dpc (days post coitum).

The embryos were obtained from crossing of FVB mice obtained from the laboratory Transgénése et Archivage d'Animaux Modéles—UPS44 (TAAM) CNRS Orleans.

After primary culture on PRIMARIA® plates (FALCON®, Becton and Dickinson) in RPMI ("Roswell Park Memorial Institute medium"), the cells were left to grow and the resultant cultures were immortalized as described above for the immortalization of human cells after 4 days, using a plasmid containing the large antigen T SV40 large and cationic liposomes.

Geneticin-resistant clones were obtained and selected. Various clones were developed and characterized on the basis of the expression of markers of endothelial cells.

Starting from these clones, two immortalized lines were obtained and were used for supplementary experiments, namely:

MAgEC 10.5: for aorta-gonad mesonephros endothelial cells of mouse embryos 10.5 dpc ("Mouse Aorta-Gonad Mesonephros Endothelial Cells" SV40 large T-antigen immortalization)

MAgEC 11.5: for aorta-gonad mesonephros endothelial cells of mouse embryos 11.5 dpc ("Mouse Aorta-Gonad Mesonephros Endothelial Cells" (SV40 large T-antigen immortalization))

The cells were cultivated in an incubator at 37° C. with a humidified atmosphere comprising 5% $CO_2$, 21% $O_2$.

All the cell lines were cultivated in OPTIMEM® medium (marketed by Gibco, France) supplemented with 2% of FBS (marketed by PAA, Austria), 0.2% of FUNGIZONE® (250 mg/ml, marketed by Gibco, France) and 1% of penicillin-streptomycin (10 000 units/ml, marketed by Gibco, France).

A.2 Characterization of the Cells

A.2.1. Analysis of Gene Expression by Reverse Transcription and Polymerase Chain Reaction (RT-PCR)

The total RNA was isolated with a Qiagen RNEASY® Kit according to the supplier's protocol. 750 ng or 1000 ng was loaded for a standard reaction of reverse transcription using oligo-dT primers.

The expression of various genes was observed, in particular the genes coding for the chemokine (C-X-C motif) ligand 16 (CXCL16), the gene SDF-1, the gene coding for the chemokine (C-X3-C motif) ligand 1 (CX3CL1), the gene coding for the chemokine 6 cysteine (6CKine), the CTACK gene, the gene coding for the kinase insert domain receptor (Kdr), the gene coding for the tyrosine kinase receptor for the endothelial growth factors c and d ((Flt4) tyrosine kinase receptor for vascular endothelial growth factors C and d"), the gene coding for the receptor of the chemokine (CC motif) (CCR7), the gene coding for the chemokine (C-X3-C motif) receptor 1 ($CXC_3CR1$). The polymerase chain reactions (PCRs) were carried out using the primers described in Table 2 and with the following protocol (a) to (e):

(a) 95° C. - 3 min
(b) 95° C. - 45 s
(c) Hybridization temperature - 45 s  } (b), (c) and (d) repeated
(d) 72° C. - 45 s                      } 30 times (d) (30 cycles)
(e) 72° C. - 7 min

TABLE 2

| Gene | SEQ ID NO | primer | Nucleotide sequence |
|---|---|---|---|
| CXCL16 | 13 | Sense | 5'-AGACAGCAAGAAGCACCAGG-3 |
|  | 14 | Antisense | 5'-CCTCTCCCATGTCATCATCC-3' |
| SDF-1 | 15 | Sense | 5'-GTTCTTCGAGAGCCACATCG-3' |
|  | 16 | Antisense | 5'-ATGGCGGAGTGTCTTTATGC-3' |

TABLE 2-continued

| Gene | SEQ ID NO | primer | Nucleotide sequence |
|---|---|---|---|
| CX3CL1 | 17 | Sense | 5'-TGCGACAAGATGACCTCACG-3 |
|  | 18 | Antisense | 5'-ATCCTGTGCCTCGGAAGTTG-3' |
| 6CKine | 19 | Sense | 5'-GGACTGCTGCCTTAAGTACAGC-3' |
|  | 20 | Antisense | 5'-GCTATCCTCTTGAGGGCTGTG-3' |
| CTACK | 21 | Sense | 5'-GGCTGAGTGAGTGAGCATGATGG-3' |
|  | 22 | Antisense | 5'-GGGATGAACACAGACACTGC-3' |
| Kdr | 23 | Sense | 5'-AGAGTGTGTCCCTGTTGTGC-3' |
|  | 24 | Antisense | 5'-GGGGTAGGATTTCCAGATGC-3' |
| Flt4 | 25 | Sense | 5'-GAGTGACTCCCTGGAGATGC-3' |
|  | 26 | Antisense | 5'-TAGCCCGTCTTGATGTCTGC-3' |
| Ccr 7 | 27 | Sense | 5'-AAACCCAGGAAAAACGTGC-3' |
|  | 28 | Antisense | 5'-RGTAGACGCCAAAGATCCAGG-3' |
| CXC3R1 | 29 | Sense | 5'-TCTTCATCACCGTCATCAGC-3' |
|  | 30 | Antisense | 5'-GATGCGGAAGTAGCAAAAGC-3' |

The hybridization temperature of the primers described in Table 2 was 57° C.

The products resulting from this RT-PCR were deposited in a migration gel in order to identify whether the gene is expressed.

ELISA Assay

All the ELISA assays were performed with the R&D SYSTEMS® ELISA DUOSET® according to the manufacturer's protocol. After collecting the cell supernatants, they were counted and the results were normalized to the cell counts.

Detection of the von Willebrand factor expressed in the cytoplasm, in the Weibel Palade plates, of the angiotensin converting enzyme present in the nuclear membrane, the cluster of differentiation CD31 and VE-cadherin was performed by fluorescence and phase-contrast microscopy equipped with DIC (Zeiss, AXIOVERT® 200).

A.2.3. Secretion of Cytokines by the Cell Lines

The CBA® method ("Cytometric Bead Array") marketed by the company Becton-Dickinson, USA, the LSR® flow cytometer marketed by BD, USA and the FCAP ARRAY® Software marketed by BD, USA were used for determining the levels of KC, TNFα, IFNγ, GM-CSF, IL-13, IL-4, IL-6, IL-10, IL-12 collected from the supernatant according to the supplier's protocol. Five logistic parametric curves were adjusted to standard samples and the results were normalized to the number of cells.

The production of VEGF, and of chemokines CXCL12, CCL17 and CXCL1 by the cell lines MAgEC 10.5 and 11.5 was also investigated.

A.2.4. Immunolabeling of the Cell Lines

The LSR® flow cytometer marketed by BD was used for determining the fluorescence and the cellular labeling. The FLOWJO® software v.5.7.2 was used for analyzing the results.

For labeling, the cells were washed with a solution of cPBS/0.5% BSA/0.1% sodium azide, detached with 1 mg/mL of type I collagenase marketed by the company Gibco, Invitrogen, fixed and permeabilized with CYTOFIX/CYTOPERM® marketed by BD, USA according to the supplier's protocol. $5 \times 10^5$ cells were taken per tube and labeled with a primary antibody in a volume of 30 μl of cPBS, 0.1% BSA for at least 45 min at 4° C. The cells were washed twice, suspended in 300 μl of cPBS and analyzed by FACS. The antibodies used are shown in Table 3 below:

TABLE 3

| | | Companies | Catalog number | Dilution |
|---|---|---|---|---|
| Primary antibody | Polyclonal from rabbit | Abcam | Ab3470 | 1/100 |
| | Monoclonal from mouse | Abcam | Ab13248 | 1/100 |
| | Polyclonal from goat | R and D | AF3776 | 1/100 |
| Control isotype | IgG from rabbit | Sigma | I87765 | 0.016 |
| | IgG from mouse | Sigma | I5381 | 0.020 |
| | IgG from goat | Sigma | I5256 | 0.020 |
| Secondary antibody | Ass anti-rabbit PE | Immuno Research | 711-116-152 | 1/100 |
| | Goat anti-mouse PE | Santa-Cruz | SC-3738 | 1/100 |
| | Rabbit anti-goat PE | Santa-Cruz | SC-3755 | 1/100 |

B Results

B.1 General Characterization of the Cells

The gels of mRNA transcripts from the products obtained with RT-PCR showed that the cells expressed the genes CXCL16, SDF-1, CX3CL1, 6CKine, CTACK (data not supplied).

The gel resulting from PCR showed that the cells of the MAgEC 11.5 line expressed the genes Kdr, Flt4 and CCR7 (columns 2, 4, 8, 10, 14 and 16, FIG. 16). The cells of the MAgEC 10.5 line expressed the gene Kdr (columns 1 and 2, FIG. 16).

Figure 8:
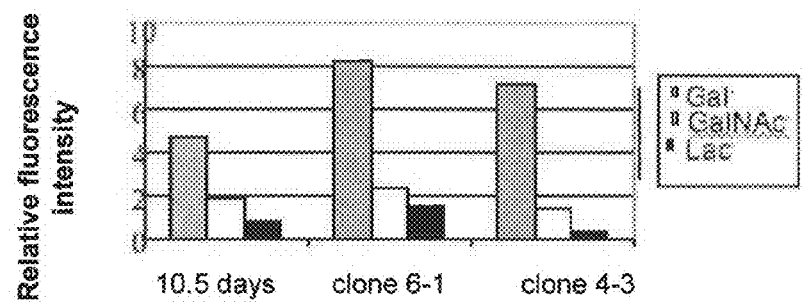
FIG. 8 is a bar chart showing the expression of galectins as a function of time. The ordinate shows the relative intensity of fluorescence corresponding to the expression level and the abscissa shows time.
Figure 9:
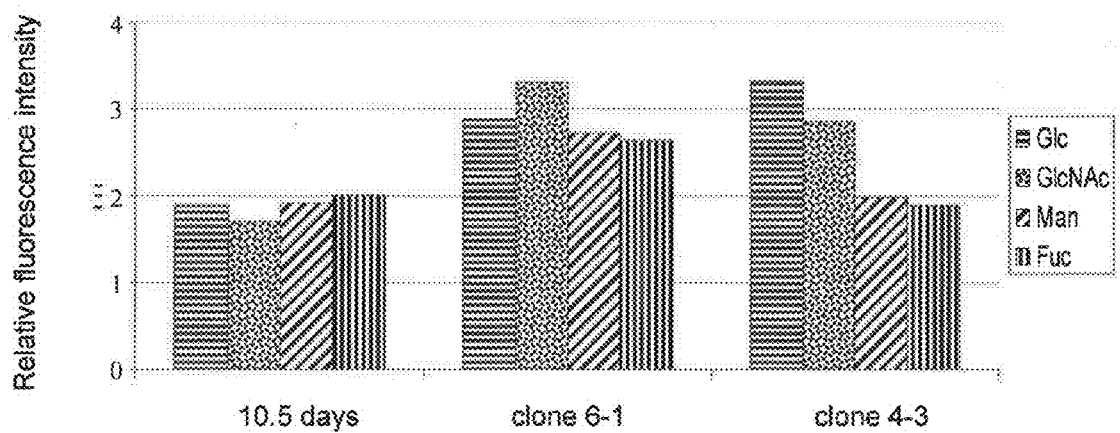
FIG. 9 is a bar chart showing the interaction of collectins with groups containing residues of the glucose (Glc-), glucose N acetyl (GlcNAc-), mannose (Man-) and fucose (Fuc-) type. The ordinate shows the relative intensity of fluorescence corresponding to the expression level and the abscissa shows time.
Figure 10:
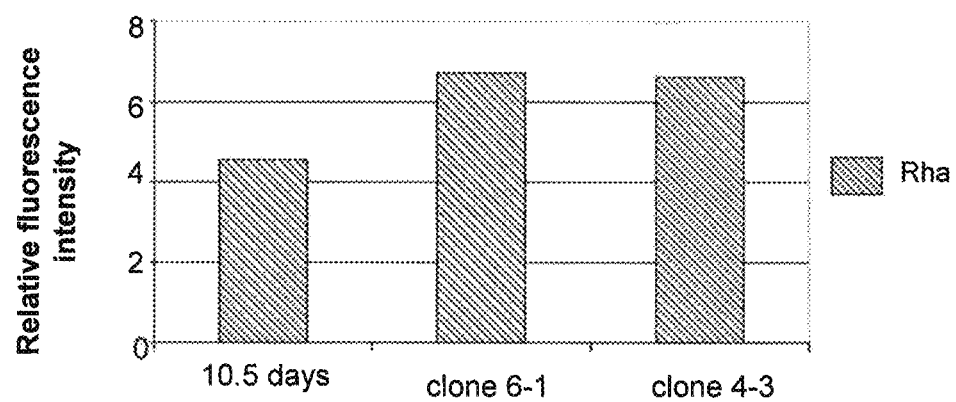
FIG. 10 is a bar chart showing the interaction of lectin with rhamnose as a function of time. The ordinate shows the relative intensity of fluorescence corresponding to the expression level and the abscissa shows time.
Figure 11:
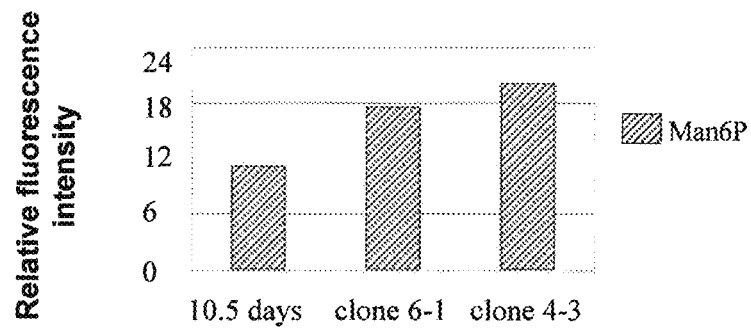
FIG. 11 is a bar chart showing the expression of the mannose 6-phosphate receptor on the cells. The ordinate shows the relative intensity of fluorescence corresponding to the expression level and the abscissa shows time.

As shown in FIG. 8, which presents photographs of ELISA assays, all the cells isolated according to the protocol described above express the markers vWf, ACE, and CD31 as presented in example 1 above. The cells also express VE-cadherin, which is a differentiation marker of endothelial cells. This example therefore clearly demonstrates that the cells obtained are feline endothelial cell precursor cells.

Figure 18:
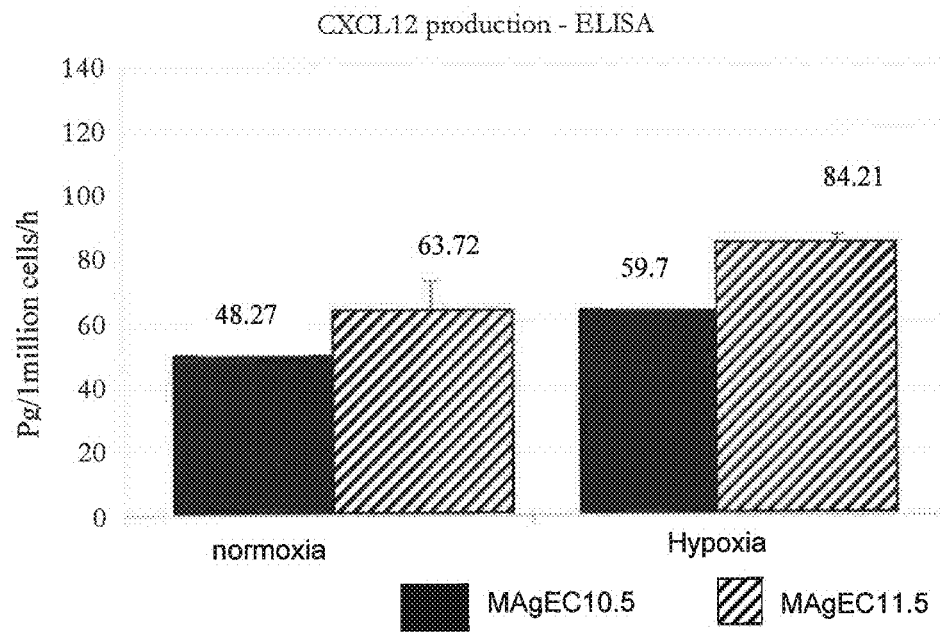
FIG. 18 is a bar chart showing production of CXCL12 measured by ELISA, by the cell lines MAgEC 10.5 (in black) and 11.5 (cross-hatched) as a function of conditions of normoxia or hypoxia. The ordinate shows the amount of VEGF determined after establishing a calibration curve, in pg (picograms) per million cells and the abscissa shows the conditions of normoxia or hypoxia.
Figure 19:
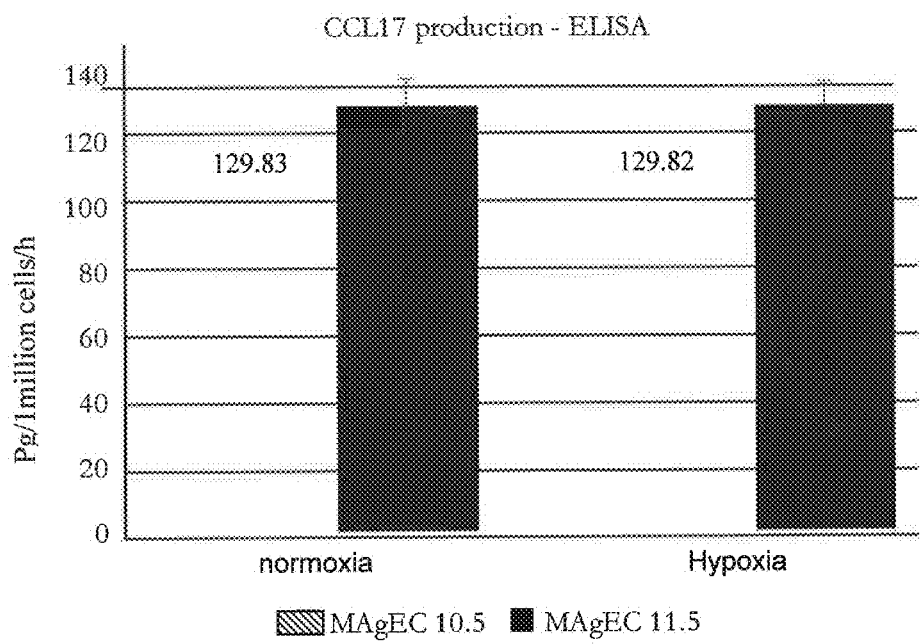
FIG. 19 is a bar chart showing production of CCL17 measured by ELISA by the cell lines MAgEC 10.5 (cross-hatched) and 11.5 (in black) as a function of conditions of normoxia or hypoxia. The ordinate shows the amount of VEGF determined after establishing a calibration curve, in pg (picograms) per million cells and the abscissa shows the conditions of normoxia or hypoxia.
Figure 20:
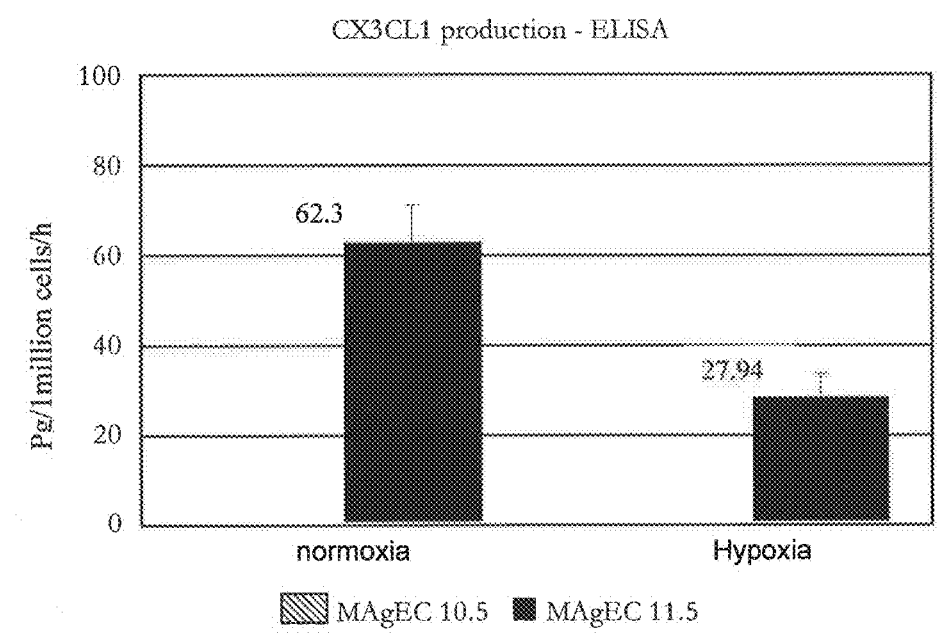
FIG. 20 is a bar chart showing production of CXCL1 visualized by ELISA by the cell lines MAgEC 10.5 (cross-hatched) and 11.5 (in black) as a function of conditions of normoxia or hypoxia. The ordinate shows the amount of VEGF determined after establishing a calibration curve, in pg (picograms) per million cells and the abscissa shows the conditions of normoxia or hypoxia.

Moreover, as shown in FIGS. 17 to 20, the cell lines MAgEC 10.5 and 11.5 do not express the chemokine CCL27 (results not shown) and produce the chemokine CXCL12 (FIG. 18). The cell line MAgEC 10.5 does not produce VEGF, CCL17, CCL27 and CXCL1 (FIGS. 17, 19 and 20). Expression of CCL17 is constant in the cells of the MAgEC 11.5 line regardless of the conditions (hypoxia or normoxia) whereas production of CXCL1 is reduced when the cells are in hypoxic conditions.

B.2 Expression Profiles of Lectins

FIGS. 9 to 12, showing the intensity of fluorescence as a function of the cells, clearly demonstrate that the expression of molecules of the galectin and collectin type changes during the development stage. The expression level increases from the cells 10.5 dcp up to a peak for clones 6-1 (11.5 dcp) and a decrease in the cells of clones 4-3 (11.5 dcp). As is shown by the results obtained, the expression level of the rhamnose-binding lectins does not change between the undifferentiated cells of clones 6-1 and the differentiated cells of clones 4-3. These results therefore clearly demonstrate that the specific receptors of mannose-6P are distributed ubiquitously among the cells of the invention.

B.3. Immunolabeling

Figure 12:
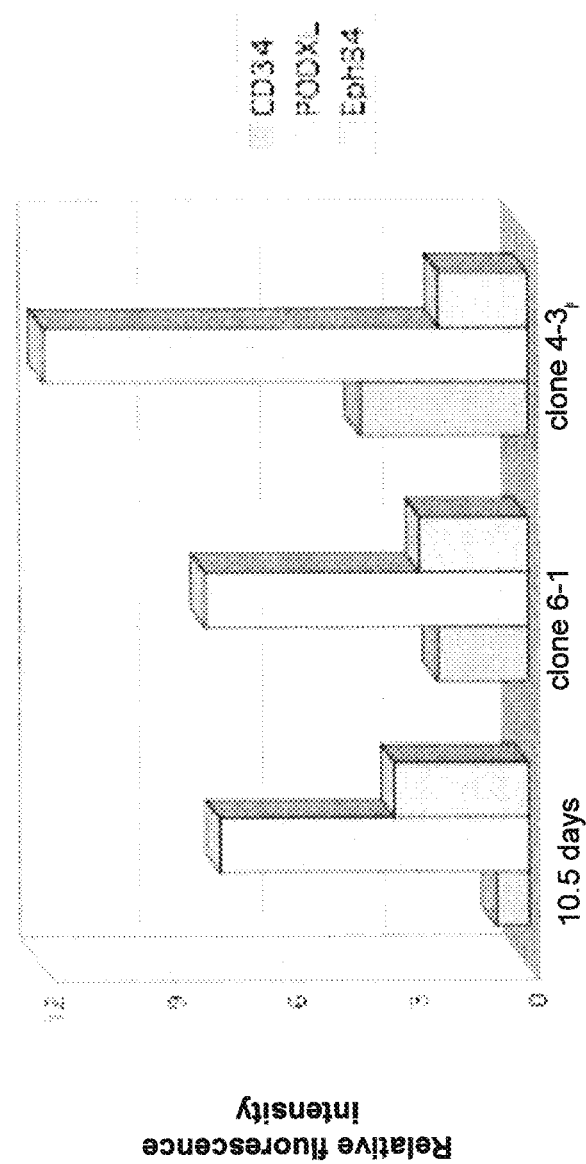
FIG. 12 is a bar chart showing the expression of the markers CD34, of the podocalyxin type (PODXL: "podocalyxin-like") and the ephrin type B receptor 4 (EphB4) as a function of the cells. The ordinate shows the relative intensity of fluorescence and the abscissa shows the cells tested.
Figure 13:
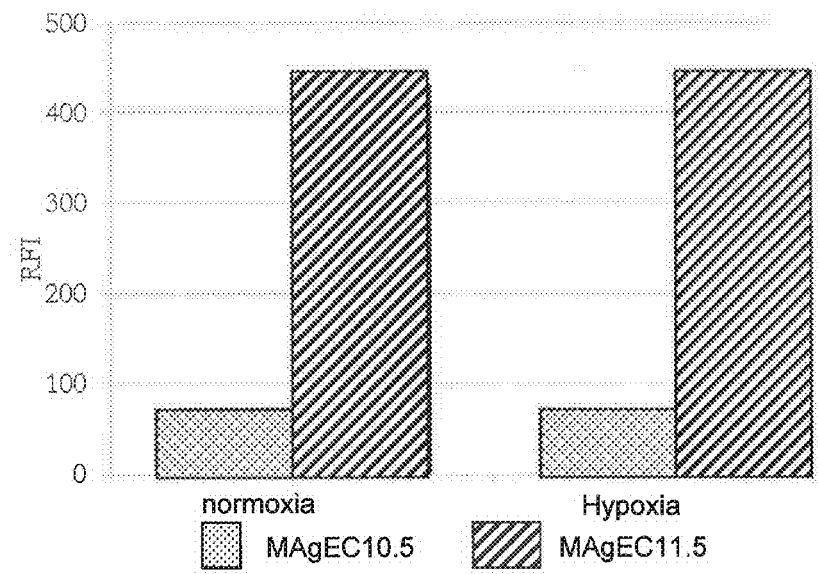
FIG. 13 is a bar chart showing the expression of the marker CCR5 in the cell lines MAgEC 10.5 (dotted lines) and 11.5 (cross-hatched) measured by flow cytofluorometry as a function of conditions of normoxia or hypoxia. The ordinate shows the relative intensity of fluorescence and the abscissa shows the conditions of normoxia or hypoxia.
Figure 14:
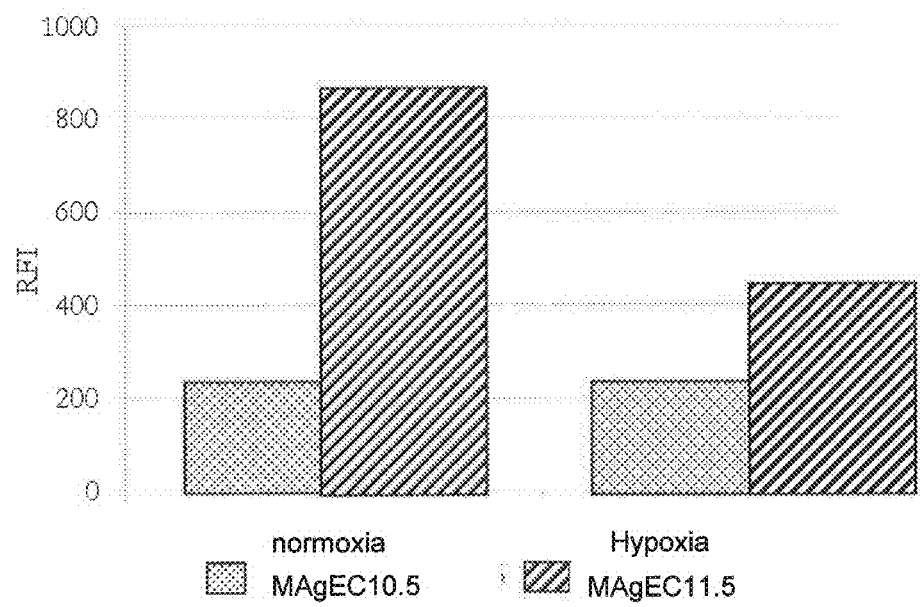
FIG. 14 is a bar chart showing the expression of the marker CCR10 in cell lines MAgEC 10.5 (dotted lines) and 11.5 (cross-hatched) as a function of conditions of normoxia or hypoxia, measured by flow cytofluorometry. The ordinate shows the relative intensity of fluorescence and the abscissa shows the conditions of normoxia or hypoxia.

The immunolabeling of the cells of the invention revealed the presence of the markers AGM PODXL and EphB4 derived from the cells, as shown in FIG. 12. Moreover, the cluster of differentiation CD34 was expressed increasingly from the 10.5 dpc cells to the 11.5 dpc cells.

Example 3

Screening of Molecules Permitting Identification of Molecules that can Induce Differentiation and/or Specialization of an Isolated Endothelial Cell Precursor Cell The human and murine endothelial cell precursor cells are cultured in 24-well plates (Falcon, Grenoble, France). The culture medium is OPTIMEM® marketed by the company Invitrogen supplemented with 2% of fetal calf serum (FCS) marketed by the company Hyclon, Longan, Utah, USA.

The cells are then cultivated for 24 hours and then the molecule to be screened is introduced into the culture medium.

The cells are then cultivated for a time in the range from 24 to 48 hours at a temperature of 37° C.

After culture for 2 days, the cells are observed for their viability, growth, and differentiation.

Photographs of the growing cells can be taken with the AXIOVERT® S microscope marketed by the company Zeiss Jena, Germany equipped with a FINE PIX® 5602 digital camera marketed by the company Fuji Film. The observations show that the cells have been subjected to toxicity, or activation, or differentiation, etc.

Observation of the growing cells makes it possible to demonstrate the effect of the targeted molecule.

The cells are also characterized using specific antibodies of differentiation markers, as described in example 1 above.

This characterization clearly demonstrates that the cells express markers of differentiated endothelial cells, or else produce angiogenesis, or else grow more quickly, or else develop into other lines such as adipocytes, smooth muscles, bone, etc., indicating that the screened molecule induces stimulation, apoptosis or differentiation.

Example 4

Addressing of Precursor Cells at Pathological Sites

The precursor cells used in this example are the isolated cells in the above examples 1 and 2.

In order to confirm addressing of endothelial cell precursor cells at the level of pathological sites, in the present case at the level of tumors, in vivo imaging experiments are conducted.

Tumoral mice are obtained by injecting $10^5$ cells of melanoma B16-F10 subcutaneously, above the paw, in order to form tumors. The mice used are of the C57 Bl6 race. The mice obtained constitute tumoral models.

The presence of tumors is verified by visual and instrumental measurement of tumor size.

The endothelial cell precursor cells are labeled with the dye DiD Vybrant (registered trademark) marketed by the company Molecular Probes USA.

After staining, the labeled cells are injected in the tumor-bearing mice.

The images are captured with apparatus for measurement of fluorescence in the near infrared, at the Small Animal Imaging Center (Centre d'Imagerie du Petit Animal, CIPA) CNRS, Orleans, France.

The images obtained clearly show addressing of the cells at the level of the tumors. Moreover, the results obtained show that the cells were incorporated in the tumors.

A similar experiment is carried out in mice that have undergone a myocardial infarction.

The mice used are identical to the aforementioned mice and the endothelial cell precursor cells are labeled by the method described above.

The infarction is caused by lesion of a coronary in the mouse. After the infarction, the labeled endothelial cell precursor cells are injected in the mice that have undergone an infarction. The cells are detected as indicated above.

The images obtained clearly show addressing of the cells at the level of the tumors as well as at the level of the tissues damaged by the infarction.

Moreover, the results obtained show that the cells are incorporated in the tumors and permit restoration of the damaged tissues and healing.

As this example demonstrates, the isolated endothelial cell precursor cells according to the invention target the tumors as well as the damaged tissues. Thus, these cells can be used for example for treating tissue lesions, for addressing therapeutic molecules, for example at the level of tumors and for treating genetically deficient cells.

Example 5

Targeting of Tumoral Sites and of Vessels in the Process of Formation by Endothelial Cell Precursor Cells 1. Materials and Methods
1.1 Labeling with Anionic Magnetic Nanoparticles (AMNP)

The cells for magnetic resonance imaging were labeled with AMNPs belonging to SPIO (super-paramagnetic iron oxide) and to the group of magnetic resonance contrast agents. The cells at 70% confluence were rinsed twice with 8 ml of OPTIMEM® base medium with 5 mM of sodium citrate. Then 5 ml of empty OPTIMEM® base medium with 5 mM of sodium citrate and 2 mM of ferric fluid (AMNP) was added to the culture vessel. The cells were incubated at 37° C., 5% $CO_2$ for 15 to 20 minutes. After incubation, the cells were rinsed twice with OPTIMEM® base medium comprising 5 mM of sodium citrate. The medium with citrate was withdrawn and 8 ml of OPTIMEM® base medium was added. The cells were incubated for 2 hours in a humidified incubator at 37° C., 5% $CO_2$, then the medium was changed for an OPTIMEM® complete medium. The cells were used for intravenous injections 24 hours after labeling.

1.2. PKH67 Labeling

The cells for PKH67 labeling were detached with 0.05% of trypsin EDTA (marketed by the company Gibco), blocked with OPTIMEM® complete medium. After detachment, the cells were washed twice with OPTIMEM® base medium. After the second washing, the cells were resuspended in 500 μl of Diluent C marketed by the company New England BIOLABS, then added to 500 μl of Diluent C with 4 μl of PKH67 marketed by the company Invitrogen, and incubated at 37° C. for 3 minutes. After incubation, labeling was stopped with 0.5% of BSA in cPBS (phosphate buffered saline, supplemented with 1 mM $CaCl_2$ and 0.5 mM $MgCl_2$). The cells were washed twice with saline buffer, counted with a Malassez chamber and resuspended at a concentration of $10 \times 10^6$ cells per ml.

1.3. Magnetic Resonance Imaging 10 days before imaging, $5 \times 10^5$ B16(F10) cells were injected subcutaneously in mice. B16(F10) melanoma cells were detached with 0.05% of trypsin EDTA marketed by the company Gibco, then rinsed twice with 0.9% of NaCl (weight/volume) and counted with a Malassez chamber. The cells were resuspended in 0.9% of NaCl (weight/volume) at a concentration of $10 \times 10^6$ cells per milliliter and mixed 1:1 (volume:volume) with MATRIGEL® marketed by the company BD biosciences, just before injection. Before injection, the mice were anesthetized with 2-3% of isoflurane. The limbs of the mice were shaved with an electric razor and depilated with depilatory cream (DERMO-TOLERANCE® depilatory cream, Vichy). 100 μl of MATRIGEL® was injected with $5 \times 10^5$ of B16(F10) cells per limb.

The MAgEC 11.5 cells labeled with AMNP and PKH67 or AMNP-Rhodamine were resuspended in 0.9% of NaCl (weight/volume) at a concentration of $10 \times 10^6$ cells per ml. 100 μl of suspended cells was injected intravenously either in the retro-orbital sinus or in the caudal vein of the mice with subcutaneous B16(F10) tumors. One mouse was injected with $1 \times 10^6$ MAgEC 11.5 cells fixed with 4% of paraformaldehyde (SIGMA®) (weight/volume) in PBS after incubation for 30 minutes at 37° C., and one mouse was injected with 100 μl of 0.9% of NaCl (weight/volume) as a control. The images of the mice were recorded before and 24 hours after intravenous injections with a Briker BioSpin 9.4T spectroscope.

1.4. Isolation of Tumor Cells from the Spleen, Lymph Nodes, and Lungs

The mice were sacrificed by cervical translocation. The lungs, spleen, and mesenteric lymph nodes were isolated, dilacerated with PBS and incubated with 5 mg/ml of type I collagenase marketed by the company Invitrogen for 30 minutes at 37° C. After incubation, the organs were washed with PBS and dissociated on filters and nylon gratings. After dissociation, the erythrocytes were lysed three times with distilled water. Briefly, the cells were centrifuged for 5 minutes at 1500 revolutions per minute and resuspended in one drop of PBS. 1 ml of distilled water was added to the cellular suspension. After 10 seconds, 4 ml of PBS was added to each tube. The cell pellet was resuspended in PBS.

1.5. In-Vivo Near-Infrared Fluorescence Imaging 10 days before imaging, $5 \times 10^5$ of B16(F10)-luc-eGFP cells obtained in collaboration with the medical biotechnology laboratory of the biotechnology department of the Jagellon University in Kraków were injected subcutaneously. The melanoma cells were detached with 0.05% of trypsin EDTA marketed by the company Gibco, then rinsed twice with 0.9% of NaCl (weight/volume) and counted with a Malassez chamber. The cells were resuspended in 0.9% of NaCl (weight/volume) at a concentration of $10 \times 10^6$ cells per milliliter and mixed 1:1 (volume:volume) with MATRIGEL®, just before injection. Before injection, the mouse was anesthetized with isoflurane. The limbs of the mice were shaved with an electric razor and 100 μl of MATRIGEL® comprising $5 \times 10^6$ B16(F10)-luc-eGFP cells was injected subcutaneously. 100 μl of MATRIGEL® was injected subcutaneously in two mice for the control. 24 hours before the first image, an injection was made either in a retro-orbital sinus, or in the caudal vein of the mouse with $2 \times 10^6$ cells:
a) MAgEC 11.5 live, labeled with DiD VYBRANT®
b) MAgEC 11.5 fixed, labeled with DiD VYBRANT®.

One mouse with subcutaneous B16(F10)-luc-eGFP cells was not treated. Before bioluminescence imaging, 150 mg/kg of firefly luciferin was injected intraperitoneally. The near-infrared images of the mice were obtained with a IVIS® Lumina system marketed by the company Caliper every day for a period of a week beginning 24 hours with the intravenous injection. Bioluminescence imaging was performed according to the Xenogen IVIS® 50 bioluminescent protocol: luciferase labeling of a tumor in mice.

2. Results:

2.1 Efficacy of Labeling of the MAgEC Cells

Figure 21:
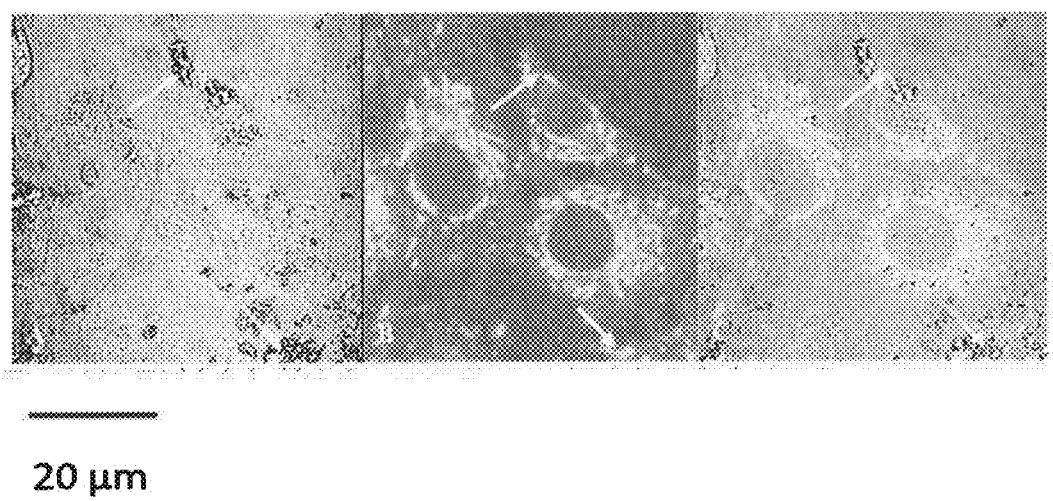
FIG. 21 shows photographs of MAgEC 11.5 cells labeled with 2 mM of AMNP particles (labeling by magnetic anionic nanoparticles) coupled to Rhodamine, A: on clear background, B: labeled with Rhodamine, C: on clear background and labeled.

FIG. 21 shows the results of labeling of the cells with AMNP nanoparticles coupled to rhodamine and shows a cytoplasmic localization of the contrast agent (FIGS. 21, A and C) indicated by the white arrows. The fluorescence was weak but sufficient (FIGS. 21 B and C). Moreover, the localization of the nanoparticles was irregular and it was located in particular around the nucleus.

The effectiveness of labeling of the MAgEC 11.5 cells with the magnetic contrast agents, in particular with AMNP particles coupled to Rhodamine 123 (MAgEC 11.5-AMNP-Rho) was measured by flow cytometry. The results obtained showed total labeling of the MAgECs, 90.4%, with the contrast agent.

Table 4 below shows the various results obtained, expressed as a percentage.

TABLE 4

| Cells | Rho− (%) | Rho+ (%) |
|---|---|---|
| MAgEC 11.5 | 99.3 | 0.33 |
| MAgEC 11.5 - AMNP-Rho | 5.72 | 90.4 |
| MAgEC 11.5 - AMNP-Rho HEPES | 4.56 | 93.7 |

Rho−: percentage of unlabeled cells
Rho+: percentage of labeled cells

Moreover, addition of HEPES, which stabilizes the pH during incubation of the cells with the AMNPs (MAgEC 11.5-AMNP-Rho HEPES), did not alter the effectiveness of labeling. Labeling was also confirmed by cellular magnetophoresis (results not supplied).

Figure 22:
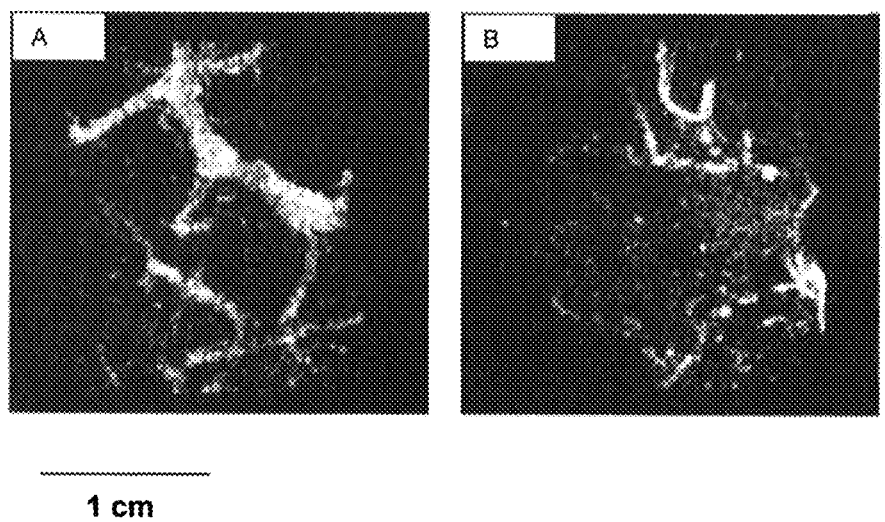
FIG. 22 shows images obtained by magnetic resonance imaging of vessels of muscles (A), of subcutaneous tumors (B).

2.2 MRI and Flow Cytometry, Demonstration of Migration of MAgECs Through a Cancerous Site 24 Hours after Intravenous Injection In this experiment, images of blood vessels were obtained by magnetic resonance imaging as described above (FIG. 22). After 7 days post-inoculation, the B16(F10) subcutaneous tumors were vascularized and thus allowed access to the injected MAgEC 11.5 cells. However, the organization of the vascular network in the tumors was not perfect (FIG. 22 A). In fact, the images of the vessels obtained for a healthy muscle (FIG. 22 A) were different from those obtained for a subcutaneous tumor (FIG. 22 B). Moreover, the background noise in FIG. 22 B indicates vascular permeability, which is a normal phenomenon in the tumoral context.

24 hours after injection of $1.0 \times 10^5$ MAgEC 11.5 cells labeled with AMNP in mice presenting B16(F10) vascular tumors, images were recorded again in order to investigate the migration of the model cells (MAgEC) to the cancer site. The images obtained (FIG. 23) had a hypodense region in the tumors of the injected and non-injected mice.

Figure 23:
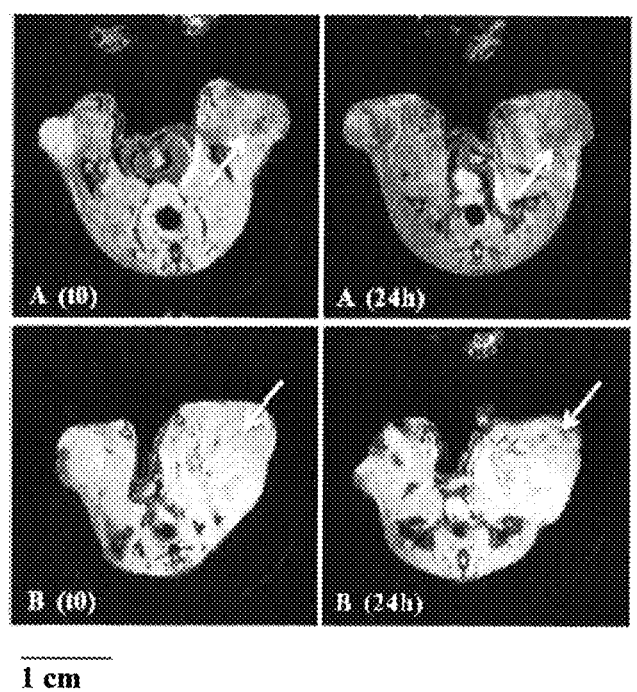
FIG. 23 shows photographs of subcutaneous tumors B16 (F10) obtained by MRI of mice before: A(t0) and 24 hours after intravenous injections of cells MagEC 11.5 labeled A(24 h), and photographs of mice not injected B(t0) and A(24 h).

Image analysis was performed by comparing the densitometry of the signal in the tumor and in the muscle. This comparison did not show a statistical difference between the mouse with and without injection of MAgEC 11.5 cells labeled with AMNP. Thus, the inventors demonstrated that the disorganized and chaotic vasculature of the tumors, in particular during rapid growth of B16(F10) subcutaneous melanomas, must be filled with deoxyhemoglobin, which gives a signal similar to the superparamagnetic iron oxide contrast agents. This changes the expected result and did not allow a difference to be observed between the two conditions. However, as shown in FIG. 23, a preferential localization of the MAgEC cells and formation of vessels by these cells was observed. Moreover, the formation of vessels by the MAgEC cells is similar to that observed during neoangiogenesis and presents a coherent, linear structure.

This experiment therefore clearly demonstrates that the precursor cells of the present invention are recruited at the level of the tumors and permit new vessel formation. Thus, these cells permit effective targeting of tumors and of tumoral angiogenesis.

In order to verify the distribution of the cells injected in the spleen, lungs, lymph nodes and tumors of animals without injection (control) and of animals with injection of MAgEC 11.5 cells, the organs were removed and were dissociated as described above. Observation of the presence of MAgEC 11.5 cells labeled with Rhodamine or with AMNP and PKH67 as described above, was undertaken by flow cytometry of the cells of the dissected organs. In all the conditions, 100 000 events were analyzed.

Figure 24:
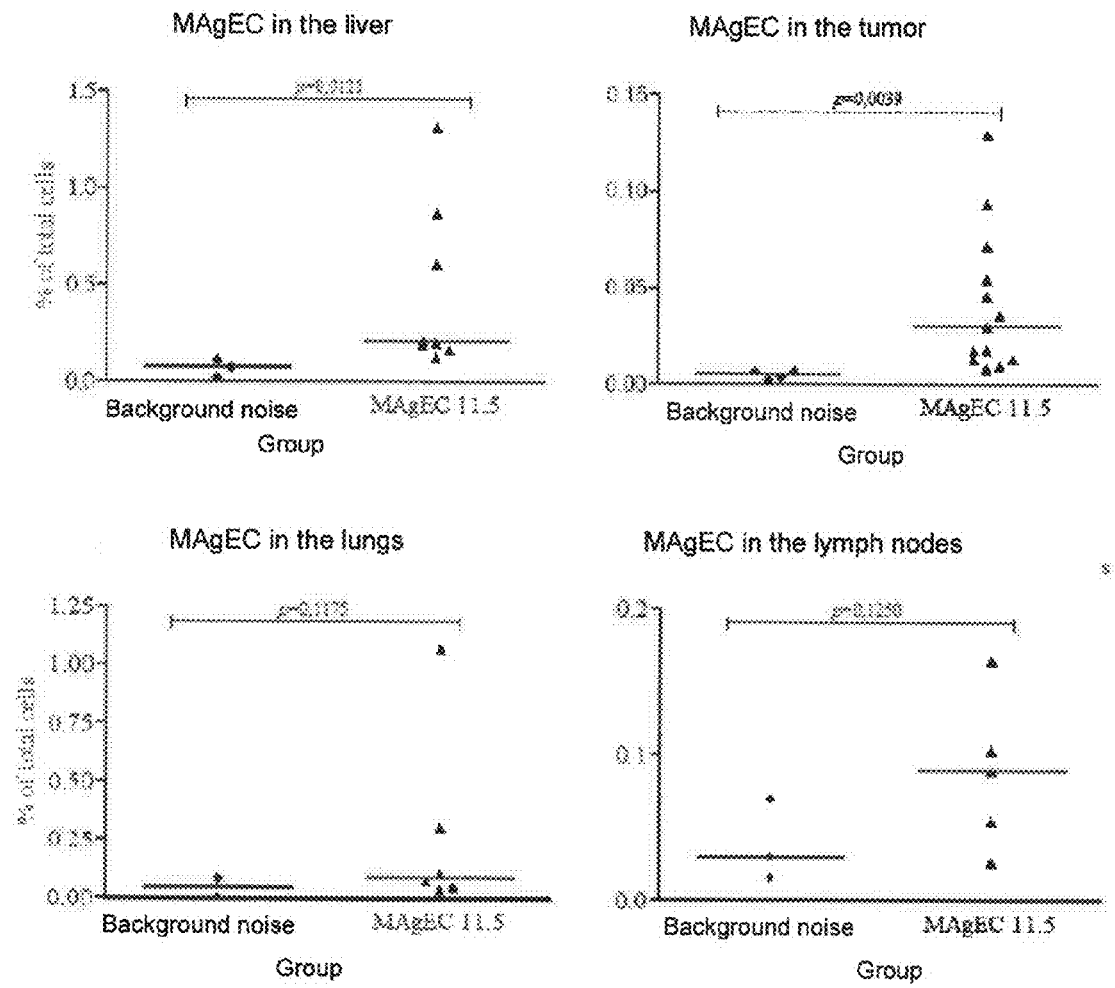
FIG. 24 shows diagrams of the percentage of total cells (abscissa) of MAgEC 11.5 in a mouse after injection of these cells in comparison with a mouse without injection (background noise) in the spleen, in a tumor, in the lungs and in the lymph nodes.

FIG. 24 shows the results obtained for each organ. In particular, a significant number of cells labeled with PK67 was found in the tumors and in the spleen compared with the background noise (fluorescence without marker), namely in the spleen: $0.47\% \pm 0.15\%$ versus $0.072 \pm 0.025\%$, p=0.0121 and in the tumor $0.42\% \pm 0.010\%$ versus $0.005 \pm 0.0012\%$, p=0.0039 (FIG. 24).

This experiment therefore clearly demonstrates that the MAgEC 11.5 cells can target tumors as well as various organs.

2.3 Localization of the MAgEC 11.5 Cells, 7 Days after Injection

The protocol employed corresponds to the protocol described above in section 1.5.

The signals obtained by DiD-labeled cells by near-infrared imaging are absorbed by melanin. Thus, during execution of this example, it was not possible to detect the MAgEC 11.5 cells in-vivo under a pigmented skin and in B16-luc-eGFP tumors. Therefore one mouse from each group was sacrificed and scanned after resection of the skin and intestines in order to reduce the fluorescence signal from chlorophyll.

In eleven mice, in which live MAgEC 11.5 cells labeled with DiD VYBRANT® had been injected, the cells were detected in the liver (11/11 mice), spleen (5/11 mice), lymph nodes (3/11 mice), lungs (2/11 mice), sternum and tibia as shown in FIGS. 25 IA, IB and IIA and IIB. Weak fluorescence was detected in the liver, spleen, lungs and sternum of the mice that were injected with fixed MAgEC 11.5 cells labeled with DiD VYBRANT®. No fluorescence was detected in the mice that were not injected (FIGS. 25 IC and IIC).

This example therefore clearly demonstrates that the cells of the invention can be used for targeting particular organs and can be used for example in methods of tissue repair, and methods for releasing active substances and/or genes in various organs.

REFERENCES

1. Arbab A S, Pandit S D, Anderson S A, et al. Magnetic resonance imaging and confocal microscopy studies of magnetically labeled endothelial progenitor cells trafficking to sites of tumor angiogenesis. Stem Cells. 2006; 24:671-678

2. de Jonge-Peeters S D, Kuipers F, de Vries E G, Vellenga E. <<ABC transporter expression in hematopoietic stem cells and the role in AML drug resistance.>> Crit Rev Oncol Hematol. 2007 June; 62(3):214-26. Epub 2007 Mar. 23.
3. Slayton W B, Li X M, Butler J, Guthrie S M, Jorgensen M L, Wingard J R, Scott E W. <<The role of the donor in the repair of the marrow vascular niche following hematopoietic stem cell transplant.>> Stem Cells. 2007 November; 25(11):2945-55
4. Dome B, Timar J, Ladanyi A, et al. Circulating endothelial cells, bone marrow-derived endothelial progenitor cells and proangiogenic hematopoietic cells in cancer From biology to therapy. Crit Rev Oncol Hematol. 2009; 69:108-1241
5. Yamahara K, Itoh H. Potential use of endothelial progenitor cells for regeneration of the vasculature. Ther Adv Cardiovasc Dis. 2009; 3:17-27.
6. Suh W, Kim K L, Kim J M, et al. Transplantation of endothelial progenitor cells accelerates dermal wound healing with increased recruitment of monocytes/macrophages and neovascularization. Stem Cells. 2005; 23:1571-1578.
7. Slayton W B, Li X M, Butler J, et al. The role of the donor in the repair of the marrowvascular niche following hematopoietic stem cell transplant. Stem Cells. 2007; 25:2945-2955
8. Shi Q, Rafli S, Wu M H, et al. Evidence for circulating bone marrow-derived endothelial cells. Blood. 1998; 92:362-367
9. Lin Y, Weisdorf D J, Solovey A, et al. Origins of circulating endothelial cells and endothelial outgrowth from blood. J Clin Invest. 2000; 105:71-77.
10. Peichev M, Naiyer A J, Pereira D, et al. Expression of VEGFR-2 and AC133 by circulating human CD34(+) cells identifies a population of functional endothelial precursors. Blood. 2000; 95:952-958.
11. Case J, Mead L E, Bessler W K, Prater D, White H A, Saadatzadeh M R, Bhavsar J R, Yoder M C, Haneline L S, Ingram DA <<Human CD34+AC133+VEGFR-2+ cells are not endothelial progenitor cells but distinct, primitive hematopoietic progenitors.>> Exp Hematol. 2007 October; 35(10):1479-80
12. Asahara T, Murohara T, Sullivan A, Silver M, van der Zee R, Li T, Witzenbichler B, Schatteman G, Isner J M. <<Isolation of putative progenitor endothelial cells for angiogenesis>> Science. 1997 Feb. 14; 275(5302):964-7
13. Szyda A, Paprocka M, Krawczenko A, et al. Optimization of a retroviral vector for transduction of human CD34 positive cells. Acta Biochim Pol. 2006; 53:815-823.
14. Kieda C, Paprocka M, Krawczenko A, Zatecki P, Dupuis P, Monsigny M, Radzikowski C, Duś D., New human microvascular endothelial cell lines with specific adhesion molecules phenotypes. Endothelium. 2002; 9(4):247-61.

The invention claimed is:

1. A human endothelial cell precursor cell selected from the cells deposited at the Collection Nationale de Cultures de Microorganismes (CNCM), under CNCM numbers 1-4220 or 1-4221.

2. A cell culture comprising the cell of claim 1.

3. The cell culture of claim 2, further comprising a growth factor.

4. The cell culture of claim 2, further comprising a molecule to be screened.

5. Cell line HucPEC 55.1, representative cells of said cell line deposited under CNCM number 1-4220.

6. Cell line HucPEC 55.2, representative cells of said cell line deposited under CNCM number 1-4221.

7. The cell culture of claim 2, further comprising a chemical molecule.

8. The cell culture of claim 2, further comprising a peptide.

9. A therapeutic composition comprising a cell of claim 1.

10. A method for treating genetically deficient cells, tissue lesions, endothelial damage, damage due to ischemia, infarction, tumors, and/or diabetes comprising administering cells of the cell line of claim 5 to an individual in need thereof.

11. A method for treating genetically deficient cells, tissue lesions, endothelial damage, damage due to ischemia, infarction, tumors, and/or diabetes comprising administering cells of the cell line of claim 6 to an individual in need thereof.

* * * * *